United States Patent
Pelzer et al.

(10) Patent No.: US 12,230,374 B2
(45) Date of Patent: Feb. 18, 2025

(54) VALUE-BASED DECISION OPTIMIZATION MODULE FOR HEALTHCARE

(71) Applicant: Clinify, Inc., Chicago, IL (US)

(72) Inventors: Nathan Pelzer, Chicago, IL (US); Eric Peebles, Chicago, IL (US)

(73) Assignee: Clinify, Inc., Chicago, IL (US)

( * ) Notice: Subject to any disclaimer, the term of this patent is extended or adjusted under 35 U.S.C. 154(b) by 0 days.

(21) Appl. No.: 18/305,596

(22) Filed: Apr. 24, 2023

(65) Prior Publication Data

US 2023/0260610 A1   Aug. 17, 2023

Related U.S. Application Data

(63) Continuation of application No. 17/104,900, filed on Nov. 25, 2020, now Pat. No. 11,676,688.

(51) Int. Cl.
*G16H 10/60* (2018.01)
*G16H 20/00* (2018.01)
*G16H 40/67* (2018.01)
*G16H 50/00* (2018.01)

(52) U.S. Cl.
CPC .............. *G16H 10/60* (2018.01); *G16H 20/00* (2018.01); *G16H 40/67* (2018.01); *G16H 50/00* (2018.01)

(58) Field of Classification Search
CPC ........ G16H 10/60; G16H 40/67; G16H 50/00; G16H 20/00
See application file for complete search history.

(56) References Cited

U.S. PATENT DOCUMENTS

| | | | |
|---|---|---|---|
| 9,536,051 B1* | 1/2017 | Kabir | G16H 50/30 |
| 10,621,164 B1 | 4/2020 | Kain | |
| 11,342,051 B1* | 5/2022 | Jain | G16H 10/60 |
| 2008/0133270 A1* | 6/2008 | Michelson | G16H 10/20 705/2 |
| 2009/0099426 A1 | 4/2009 | Sachanandani | |
| 2018/0358130 A1* | 12/2018 | Schmidt | G16H 40/20 |
| 2019/0006045 A1* | 1/2019 | Averill | G06Q 10/10 |
| 2019/0172586 A1* | 6/2019 | Choksi | G16H 10/60 |
| 2021/0050113 A1 | 2/2021 | Harle | |
| 2021/0319887 A1* | 10/2021 | Derrick, Jr. | A61B 5/7275 |
| 2022/0215910 A1* | 7/2022 | Charlson | G16H 10/60 |

* cited by examiner

*Primary Examiner* — Mohamed Charioui
*Assistant Examiner* — Christine Y Liao
(74) *Attorney, Agent, or Firm* — McDermott Will & Emery LLP

(57) ABSTRACT

A method including retrieving an information for a subject, the information comprising a disease of the subject, a subject condition, and a previous condition. The method includes parsing a contract between a provider and a payor to identify a measurable value and identifying a contract success factor and a social determinant for the disease in the subject based on the subject condition, the measurable value, the previous condition, and the contract. The method also includes identifying multiple options available for the provider in a treatment of the disease in the subject. The method also includes identifying an expected condition based on the performance parameter and on the disease of the subject, and providing a recommendation to the provider for an action to improve the expected condition. A system and a non-transitory, computer-readable medium storing instructions to perform the above method are also provided.

20 Claims, 15 Drawing Sheets

TABLE 2

| | | | | | | | | | |
|---|---|---|---|---|---|---|---|---|---|
| 60639 | 1906.01 | 10.00% | 12.40% | 26.90% | 33.10% | 25.90% | 79.6 | -5.8 | 16.50% |
| 60639 | 1906.02 | 10.30% | 12.40% | 28.20% | 32.60% | 26.60% | 75.8 | -8.7 | 17.20% |
| 60639 | 1907.01 | 10.30% | 13.50% | 26.60% | 34.60% | 24.90% | 77.4 | -21.9 | 18.50% |
| 60639 | 1907.2 | 11.10% | 15.20% | 27.70% | 36.40% | 22.90% | 80.5 | -18.8 | 21.10% |
| 60639 | 1908 | 10.80% | 13.40% | 27.50% | 34.60% | 24.70% | 82.1 | -20.6 | 18.20% |
| 60639 | 1909 | 12.80% | 12.90% | 30.90% | 35.10% | 24.10% | 82 | -24.6 | 17.70% |
| 60639 | 1910 | 11.50% | 13.90% | 28.60% | 35.40% | 22.60% | 77.4 | -8.6 | 18.40% |
| 60639 | 1911 | 11.30% | 14.70% | 27.50% | 36.50% | 22.00% | 79.2 | -21.5 | 19.80% |
| 60639 | 1912 | 11.50% | 16.70% | 26.90% | 38.50% | 19.60% | 76 | -19.1 | 22.60% |
| 60639 | 1913.01 | 12.40% | 14.70% | 30.30% | 36.60% | 21.70% | 77.1 | -20 | 19.90% |
| 60639 | 1913.02 | 11.70% | 15.00% | 28.00% | 37.30% | 21.40% | 80.3 | -14.7 | 20.50% |
| 60639 | 2002 | 12.10% | 14.10% | 28.50% | 36.60% | 22.10% | 78.5 | -18.6 | 18.90% |
| 60639 | 2003 | 12.70% | 15.50% | 29.50% | 37.90% | 20.60% | 76 | -11.8 | 20.90% |
| 60639 | 2004.01 | 12.10% | 15.70% | 29.50% | 37.40% | 21.00% | 75.6 | -30.4 | 21.00% |
| 60639 | 2004.02 | 11.30% | 13.90% | 26.80% | 36.40% | 22.00% | * | -24.1 | 18.10% |
| 60639 | 2305 | 13.70% | 15.10% | 31.10% | 38.90% | 20.10% | 75.6 | -32.1 | 20.10% |
| 60639 | 2502 | 14.80% | 14.80% | 38.90% | 41.40% | 21.40% | 75.7 | -20.2 | 22.50% |
| 60639 | 2503 | 15.70% | 15.40% | 41.30% | 43.70% | 20.30% | 74.3 | -32.5 | 23.50% |
| 60639 | 2504 | 15.20% | 14.10% | 43.20% | 42.80% | 22.90% | 76.1 | -24.8 | 22.00% |
| 60639 | 8312 | 11.20% | 13.90% | 26.90% | 35.60% | 22.90% | 76 | -21.9 | 18.10% |
| STANDARD DEVIATION | | 1.58% | 1.10% | 4.81% | 2.83% | 1.88% | 2.28 | 7.21 | 1.92% |
| MEAN | | 12.1% | 14.4% | 30.2% | 37.1% | 22.5% | 77.64 | (20.04) | 19.78% |
| +1 STANDARD DEVIATION | | 13.7% | 15.5% | 35.0% | 39.9% | 24.3% | 79.92 | (12.82) | 21.69% |
| -1 STANDARD DEVIATION | | 10.55% | 13.27% | 25.43% | 34.24% | 20.57% | 75.36 | (27.25) | 17.86% |

KEY

BEST OUTCOMES

ONE STANDARD DEVIATION FROM THE MEAN

WORST OUTCOMES

VALUE-BASED DECISION OPTIMIZATION MODULE FOR HEALTHCARE

CROSS-REFERENCE TO RELATED APPLICATIONS

The present disclosure is related and claims priority under 35 U.S.C. § 120 as a Continuation Application to U.S. Ser. No. 17/104,900, filed on Nov. 25, 2020, entitled VALUE-BASED OPTIMIZATION MODULE FOR HEALTHCARE, to Pelzer, et al. the contents of which are hereby incorporated by reference in their entirety, for all purposes.

BACKGROUND

Field

The present disclosure generally relates to methods and systems for providing healthcare recommendations resulting in improved outcomes for patients. More specifically, embodiments as disclosed herein are related to a system to provide clinical decision transparency at the point-of-care and proactively make recommendations to healthcare providers to make optimized healthcare decisions.

Description of the Related Art

Current clinical decision support platforms provide non-actionable data, typically aggregated statistically and therefore non-specific to individual practices. As a result, the conclusions and reports from such platforms have little impact and value for cases where a physician or healthcare practitioner may look for concrete steps or actions to improve a healthcare output for a specific patient.

SUMMARY

In one embodiment of the present disclosure, a computer-implemented method includes retrieving, from a record in a remote server, an information for a subject, the information including a disease of the subject, a subject condition, and a previous condition of the subject. The computer-implemented method includes parsing a digital version of a contract between a provider and a payor to identify a measurable value using a context-based language scanner, determining the measurable value based on a value for the subject condition, and identifying a contract success factor and a social determinant for the disease in the subject based on the subject condition, the measurable value, the previous condition of the subject, and the contract. The computer-implemented method includes identifying multiple options available for the provider in a treatment of the disease in the subject, displaying, in a graphic display for a user, at least one of the options and evaluating a performance parameter for the provider based on the subject condition. The computer-implemented method also includes identifying an expected condition for the subject based on the performance parameter and on the disease of the subject and providing a recommendation to the provider for an action to improve the expected condition for the subject.

According to one embodiment, a system is described that includes one or more processors and a memory coupled with the processor, the memory including instructions that, when executed by the one or more processors, cause the system to retrieve, from a record in a remote server, an information for a subject, the information including a disease of the subject, a subject condition, and a previous condition of the subject. The one or more processors also execute instructions to parse a digital version of a contract between a provider and a payor to identify a measurable value using a context-based language scanner, to determine the measurable value based on a value for the subject condition, and to identify a contract success factor and a social determinant for the disease in the subject based on the subject condition, the measurable value, the previous condition of the subject, and the contract. The one or more processors also execute instructions to identify multiple options available for the provider in a treatment of the disease in the subject, to display, in a graphic display for a user, at least one of the options and to evaluate a performance parameter for the provider based on the subject condition, to identify an expected condition for the subject based on the performance parameter and on the disease of the subject, and to provide a recommendation to the provider for an action to improve the expected condition for the subject.

According to one embodiment, a non-transitory, machine-readable medium is described that includes instructions, which when executed by one or more processors, cause a computer to perform a method that includes retrieving, from a record in a remote server, an information for a subject, the information including a disease of the subject, a subject condition, and a previous condition of the subject. The method includes parsing a digital version of a contract between a provider and a payor to identify a measurable value using a context-based language scanner, determining the measurable value based on a value for the subject condition, and identifying a contract success factor and a social determinant for the disease in the subject based on the subject condition, the measurable value, the previous condition of the subject, and the contract. The method includes identifying multiple options available for the provider in a treatment of the disease in the subject, displaying, in a graphic display for a user, at least one of the options and evaluating a performance parameter for the provider based on the subject condition. The method also includes identifying an expected condition for the subject based on the performance parameter and on the disease of the subject and providing a recommendation to the provider for an action to improve the expected condition for the subject.

In yet another embodiment, a system is described that includes a means for storing commands and a means for executing the commands causing the system to perform a method that includes retrieving, from a record in a remote server, an information for a subject, the information including a disease of the subject, a subject condition, and a previous condition of the subject. The method includes parsing a digital version of a contract between a provider and a payor to identify a measurable value using a context-based language scanner, determining the measurable value based on a value for the subject condition, and identifying a contract success factor and a social determinant for the disease in the subject based on the subject condition, the measurable value, the previous condition of the subject, and the contract. The method includes identifying multiple options available for the provider in a treatment of the disease in the subject, displaying, in a graphic display for a user, at least one of the options and evaluating a performance parameter for the provider based on the subject condition. The method also includes identifying an expected condition for the subject based on the performance parameter and on the disease of the subject and providing a recommendation to the provider for an action to improve the expected condition for the subject.

In a further embodiment, a computer-implemented method is described, including accessing, in a remote server, a social determinant factor for a subject having a disease condition. The computer-implemented method includes requesting, from the remote server, a graphic display of a cohort of patients living in a neighborhood of the subject, identifying an opportunity to improve an expected outcome for the subject based on the graphic display, and verifying a payment option for the subject based on the opportunity and on a contract with a payor. The computer-implemented method also includes providing a recommendation to the subject for acting on the opportunity.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

In the figures, elements and steps denoted by the same or similar reference numerals are associated with the same or similar elements and steps, unless indicated otherwise.

DETAILED DESCRIPTION

In the following detailed description, numerous specific details are set forth to provide a full understanding of the present disclosure. It will be apparent, however, to one ordinarily skilled in the art, that embodiments of the present disclosure may be practiced without some of these specific details. In other instances, well-known structures and techniques have not been shown in detail so as not to obscure the disclosure.

General Overview

Many clinical decision support platforms provide non-actionable data insights in the form of dashboards and other reports that are not dynamic enough to capture medical and operational variables specific to individual practices. As far as we can tell, there doesn't seem to be a platform that is specific to enabling performance in value-based care and that provides clinical decision transparency at the point-of-care (e.g., within the electronic health record). Furthermore, our platform takes clinical decision-making further by identifying situations in which physicians make good or bad decisions, and then proactively making recommendations to the physician on how to make optimized decisions based on the various situations they find themselves in throughout the clinical day.

The disclosed system addresses this problem specifically arising in the realm of computer technology by providing a solution also rooted in computer technology, namely, by retrieving healthcare data and social determinant data from multiple sources to provide healthcare recommendations to healthcare professionals in real-time.

Although many examples provided herein describe a patient's search inputs or healthcare history being identifiable, or download history for images being stored, each patient or user may grant explicit permission for such healthcare information to be shared or stored. The explicit permission may be granted using privacy controls integrated into the disclosed system. Each patient may be provided notice that such healthcare information will be shared with explicit consent, and each patient may at any time terminate the information sharing, and may delete any stored healthcare information. The stored patient information may be encrypted to protect patient security and privacy.

Example System Architecture

Figure 1:
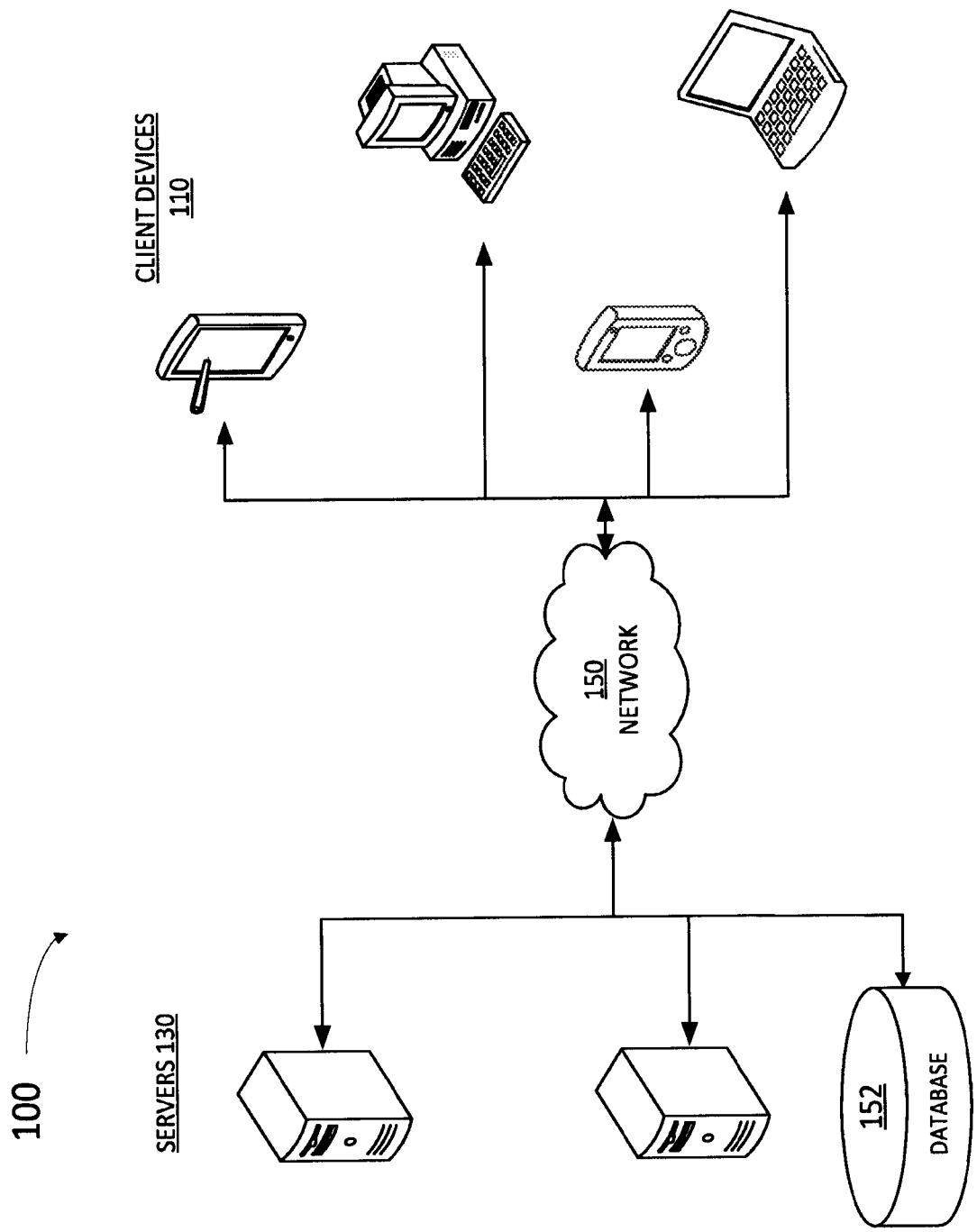
FIG. 1 illustrates an example architecture for a value-based decision optimization module, according to some embodiments.

FIG. 1 illustrates an example architecture 100 for a system for practicing some implementations of the disclosure.

Architecture 100 includes servers 130, a database 152, and client devices 110 coupled over a network 150. One of the many servers 130 is configured to host a memory, including instructions which, when executed by a processor, cause the server 130 to perform at least some of the steps in methods as disclosed herein. In some embodiments, the memory may be external to the server, e.g., database 152. In some embodiments, architecture 100 is configured to present a menu with multiple recommendations for actions to take by a physician or healthcare provider, who may be the user of client device 110, to a patient who may be suffering from a disease or condition. The recommendations may be generated from a patient history in a healthcare record, which may be stored in a clinical history log in a memory of the server, or in a database communicatively coupled with network 150.

Servers 130 may include any device having an appropriate processor, memory, and communications capability for hosting the clinical history log, a social database, and a clinical decision engine. The clinical decision engine may be accessible by various clients 110 over network 150. Client devices 110 may include, for example, desktop computers, mobile computers, tablet computers (e.g., including e-book readers), mobile devices (e.g., a smartphone or PDA), or any other devices having appropriate processor, memory, and communications capabilities for accessing the clinical history log on one or more of servers 130 or a database. Network 150 can include, for example, any one or more of a local area network (LAN), a wide area network (WAN), the Internet, and the like. Further, network 150 can include, but is not limited to, any one or more of the following network topologies, including a bus network, a star network, a ring network, a mesh network, a star-bus network, tree or hierarchical network, and the like.

Figure 2:
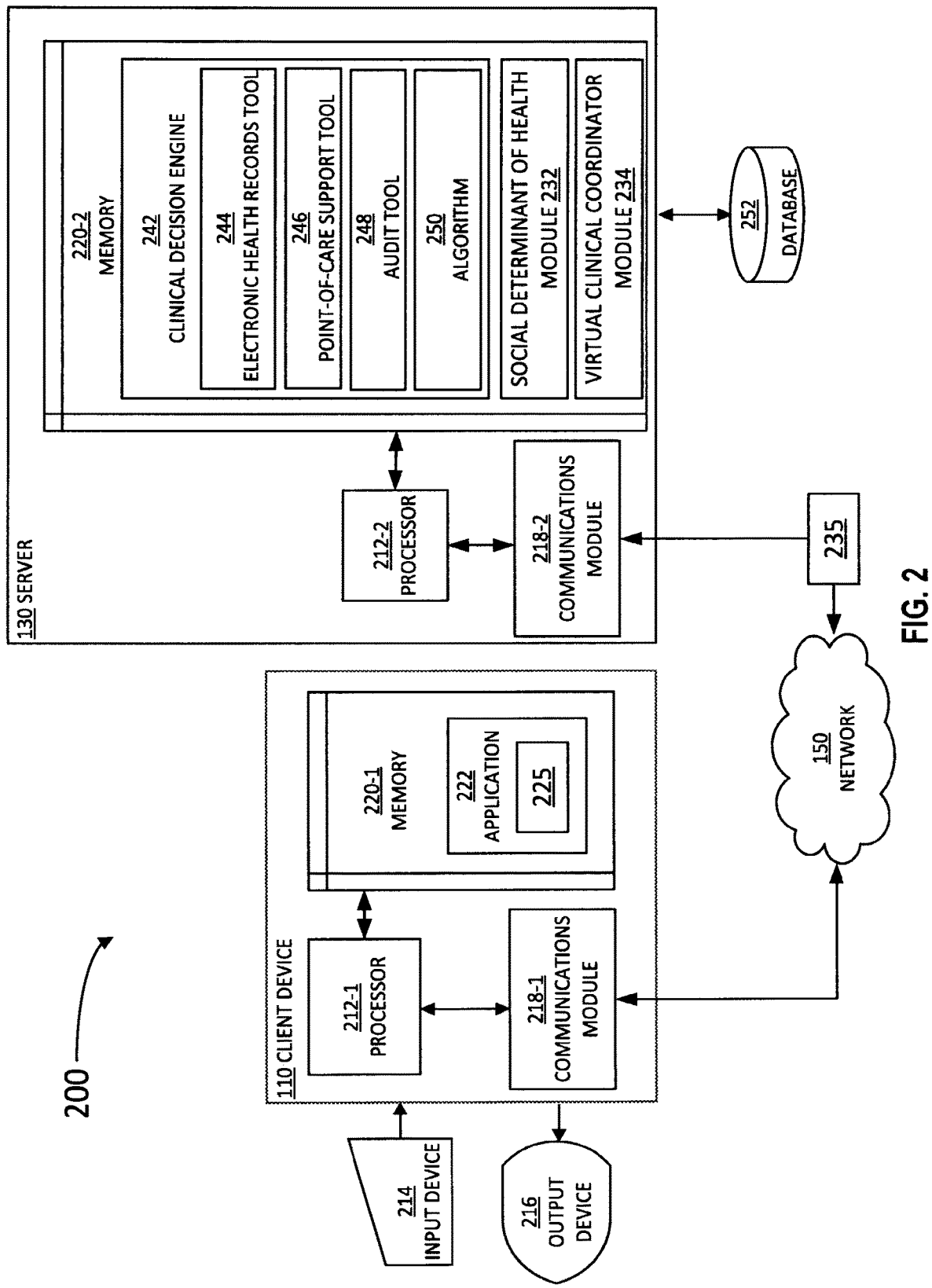
FIG. 2 is a block diagram illustrating an example server and client from the architecture of FIG. 1, according to certain aspects of the disclosure.

FIG. 2 is a block diagram 200 illustrating an example server 130 and client device 110 in the architecture 100, according to certain aspects of the disclosure. Client device 110 and server 130 are communicatively coupled over network 150 via respective communications modules 218-1 and 218-2 (hereinafter, collectively referred to as "communications modules 218"). Communications modules 218 are configured to interface with network 150 to send and receive information, such as data, requests, responses, and commands to other devices on the network. Communications modules 218 can be, for example, modems or Ethernet cards. Client device 110 may be coupled with an input device 214 and with an output device 216. Input device 214 may include a keyboard, a mouse, a pointer, or even a touch-screen display that a healthcare provider may use to interact with client device 110. Likewise, output device 216 may include a display and a speaker with which the patient may retrieve results from client device 110. Client device 110 may also include a processor 212-1, configured to execute instructions stored in a memory 220-1, and to cause client device 110 to perform at least some of the steps in methods consistent with the present disclosure. Memory 220-1 may further include an application 222, including specific instructions which, when executed by processor 212-1, cause a digital content 225 (e.g., provided remotely by server 130) to be displayed for the patient. Digital content 225 may include multiple recommendations presented to the healthcare provider by server 130, and the healthcare provider may store at least some of the recommendations from digital content 225 in memory 220-1.

Application 222 may be configured to display a digital content 225 in output device 216. Application 222 may be installed in memory 220-1 by the manufacturer, together with the installation of an operating system that controls all hardware operations of client device 110. Moreover, in some embodiments, a healthcare provider may download application 222 in client device 110 from a remote server. Digital content 225 may include a widget having interactive elements (e.g., buttons) for controlling a display of data provided by application 222 in output device 216.

Server 130 includes a memory 220-2, a processor 212-2, and a communications module 218-2. Processor 212-2 is configured to execute instructions, such as instructions physically coded into processor 212-2, instructions received from software in memory 220-2, or a combination of both. Memory 220-2 includes a clinical decision engine 242 for integrating images, videos, and other multimedia files stored in a database 252 into digital content 225. Clinical decision engine 242 may push clinical data from digital promotion database 252 to a user of client device 110 that is a healthcare provider through application 222 or a web browser installed in client device 110. Accordingly, application 222 in client device 110 may be installed by server 130 and perform scripts and other routines provided by server 130. In some embodiments, application 222 may be configured to display digital content 225 provided by clinical decision engine 242. Hereinafter, memories 220-1 and 220-2 and processors 212-1 and 212-2 will be collectively referred to as "memories 220" and "processors 212," respectively.

Clinical decision engine 242 integrates digital content 225 based on information retrieved from a clinical history log stored in a database 252. Clinical decision engine 242 may include an electronic health records tool 244. Electronic health records tool 244 hosts a panel of multiple advertisement payloads in digital content 225 to be displayed by application 222 in output device 216. In some embodiments, electronic health records tool 244 may display multiple graphs, charts, and tables for display in output device 216 through application 222.

Clinical decision engine 242 may also include a point-of-care support tool 246. Point-of-care support tool 246 is configured to include a script in digital content 225 that triggers a signal to clinical decision engine 242 when the user interacts with digital content 225, or with a specific advertisement payload therein. In some embodiments, either one or both of electronic health records tool 244 and point-of-care support tool 246 may include a plugin script configured to display buttons (e.g., click to act buttons, and the like) and other control commands in a widget included in digital content 225.

Clinical decision engine 242 may also include an audit tool 248. Audit tool 248 may be configured to verify and correlate the steps taken by the healthcare provider in the handling of a patient according to a contract established between the healthcare provider and the healthcare insurance or payor. Audit tool 248 may be configured to identify issuing steps, or actions, overcharges, undercharges, and outstanding invoices that require attention. Accordingly, audit tool 248 may provide a report for the healthcare provider and/or the insurer, including a contractual violation by either party.

Memory 220-2 may also include a social determinant of health (SDoH) module 232, and a virtual clinical coordinator (VCC) module 234. SDoH module 232 retrieves patient information from the electronic health record (e.g., from database 252) to identify a patient zip code plus four. In some embodiments, SDoH makes API calls to a number of social datasets (American Community Survey, Census, FFIEC, etc.) in a database 252, to determine what the prevalence of certain social determinants are in the specific geographic region in which a selected patient lives. Based on these values, clinical decision engine 242 runs an algorithm 250 to determine if the social determinant variable is in the lower 25% in terms of performance across the selected geographic area. When a social determinant is found to be in the lower 25% of performance, clinical decision engine 242 determines whether that variable impacts the patients' health, using algorithm 250. Accordingly, algorithm 250 associates a social determinant to clinical conditions (e.g., food insecurity will impact diabetes/hypertension patients). This information will then feed a customized report which the physician or user of the value-based decision optimization module will be able to access. The customized report allows the physician or other user to make a fully informed recommendation around the care needed to treat each specific patient.

VCC module 234 may establish a bi-directional connection to a practice electronic health record system (e.g., in database 252). In some embodiments, clinical decision engine 242 operates in the background for 30 days collecting clinical, lab, pharmacy, and patient demographic data from database 252 and storing the data in memory 220-2 or in memory 220-1, for analysis. After 30 days (or any other selected period of time), clinical decision engine 242 benchmarks the performance of the practice as it relates to standardized clinical cost and quality measures. In some embodiments, the quality measures may be selected from the Medicare Shared Savings Program measures or from any other standardized set of measures available or to be developed.

In some embodiments, clinical decision engine 242 generates and provides a benchmark report to the user, including a summary of areas where the user can focus efforts to improve the performance on cost and quality measures. In some embodiments, clinical decision engine 242 may digitize the payer (e.g., insurance company, government agency, and the like) contracts held by the provider (e.g., physician, clinic, hospital, and the like). Accordingly, clinical decision engine may establish which patients are covered under a given contract, what services are to be provided to those patients, and the available budget for reimbursement from those services.

In some embodiments, algorithm 250 compares the contract data to the practice scheduling system, and identifies which patients will be seen on a given day. Based on this information, clinical decision engine 242 pushes recommendations 235 (e.g., in real-time) to the electronic medical record (EMR) of the practitioner, based on a desired optimal contract performance and evidence-based gold standards of care for management of chronic conditions (diabetes, heart failure, obesity, and the like). Recommendations 235 may include a PDF attachment to clinical notes, or as standing orders that the physician can click-off on while still in their EMR during a patient visit.

Clinical decision engine 242 tabulates recommendations 235 as "opportunities" provided to the physician. The number of opportunities provided to the physician and the number of opportunities acted upon by the physician may be a quality factor considered for the healthcare system. In some embodiments, clinical decision engine 242 monitors situational variables such as time of day, whether the physician is behind/ahead in schedule, the complexity of patients seen by the physician, and others to identify under which situations the physicians make optimal decisions based on contract requirements, and under which situation the physician makes less than optimal decisions.

Accordingly, clinical decision engine 242 measures situation-based performance. In some embodiments, clinical decision engine 242 monitors for "like" situations to occur in the future and proactively recommend the most optimal decision for the physician, given their current situation (cf. recommendations 235). Over time, a recommender algorithm 250 is refined and updated with machine learning models. Accordingly, in some embodiments, algorithm 250 predicts with a calibrated accuracy how a physician would perform in certain alternative payment models based on their patient panel profile, their operating situation, and the requirements of the payer contracts they hold.

Database 252 includes the clinical history of multiple patients listed according to a patient identification. To achieve this, in some embodiments, an algorithm 250 stores commands which, when executed by processor 212-2, causes server 130 to integrate digital content 225. Algorithm 250 may include a neural network (NN) trained over the clinical history log in database 252, to select and process digital content 225 targeted to the specific preferences of a healthcare provider using any one of applications 222 to access a network site hosted by server 130. In some embodiments, application 222 may access a remote server hosting database 252, which may be different from a server hosting clinical decision engine 242. For example, in some embodiments, application 222 may access a remote server that holds public information in database 252. The public information may include police reports over an area that includes a residence of a patient of a healthcare provider using application 222 in client device 110. In some embodiments, the public information in database 252 may include census information regarding income, standard of living, schools, hospitals, playgrounds, grocery stores, and other geographic and socioeconomic information of a selected area of interest for a healthcare provider.

Database 252 may include a list of frequent patients of one or multiple retailers. The retailer may create, update, and maintain database 252 with patient identification data, and clinical history data. In that regard, database 252 may be hosted by a public service, a government office, or a healthcare payer, while clinical decision engine 242 may be hosted by a third party private enterprise. Accordingly, server 130 hosting electronic health records tool 244 may have access to one or more government databases, to one or more patient identification databases, and to one or more clinical history log databases, all within database 252, through contractual agreements with the owners or administrators of the desired information.

Figure 3:
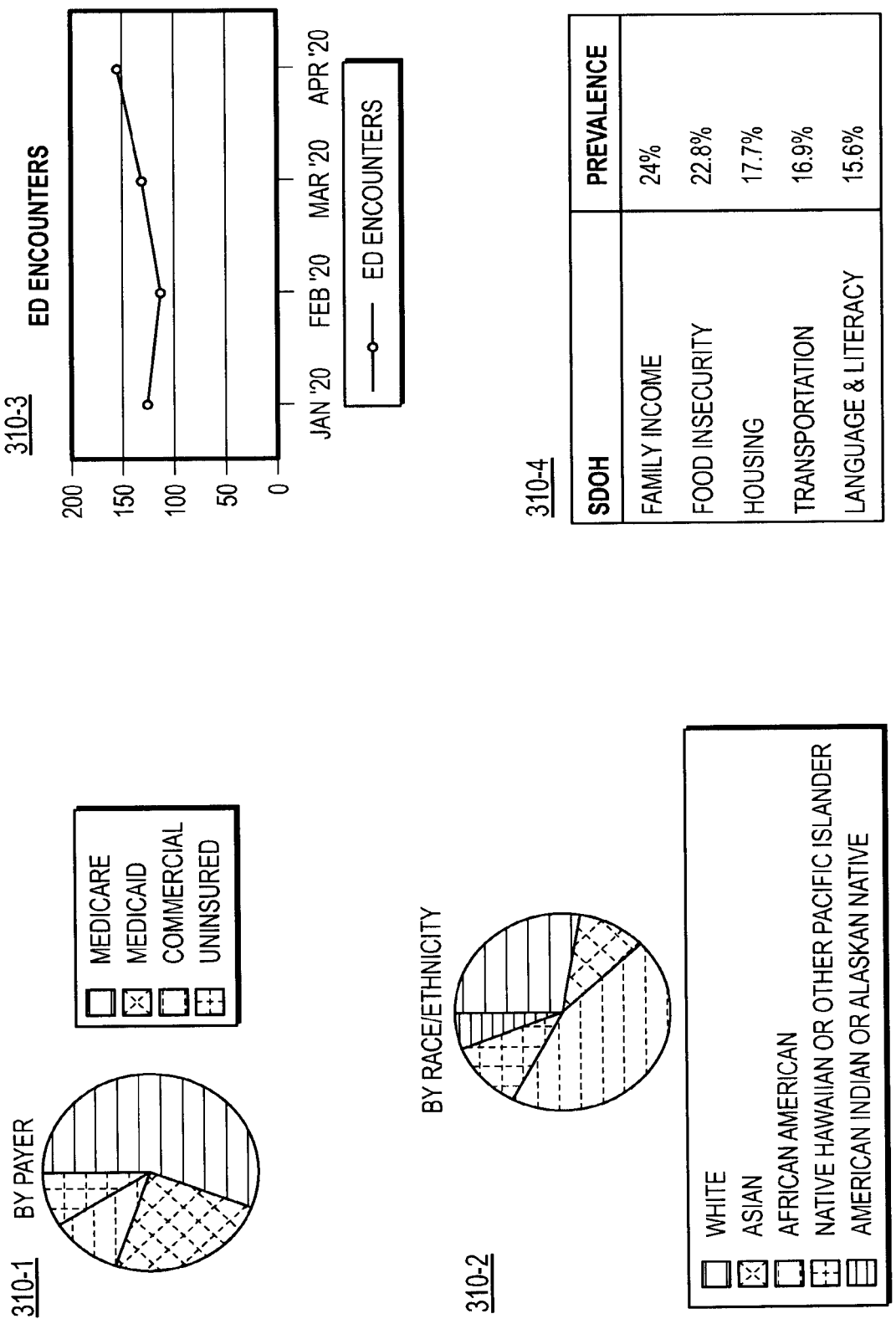
FIG. 3 illustrates screenshots of performance metrics in a healthcare system, according to some embodiments.

FIG. 3 illustrates screenshots 310-1, 310-2, 310-3, and 310-4 (hereinafter, collectively referred to as "screenshots 310") of performance metrics in a healthcare system, according to some embodiments.

Screenshot 310-1 illustrates a pie chart of a cohort of patients divided by payer (e.g., Medicare, Medicaid, commercial, and uninsured). Screenshot 310-1 is illustrative of the degree of efficiency and reach out of a healthcare facility, clinic, or initiative, within a certain community. Screenshot 310-2 is a pie chart of the cohort of patients separated by ethnicity. Screenshot 310-3 is a chart indicative of emergency department encounters through a selected span of time. Screenshot 310-4 is a table illustrating some of the most prevalent social determinants of health (SDoH, e.g., Family Home, Food Insecurity, Housing, Transportation, Language & Literacy, and the like), and the degree of incidence within the cohort of patients.

Figure 4:
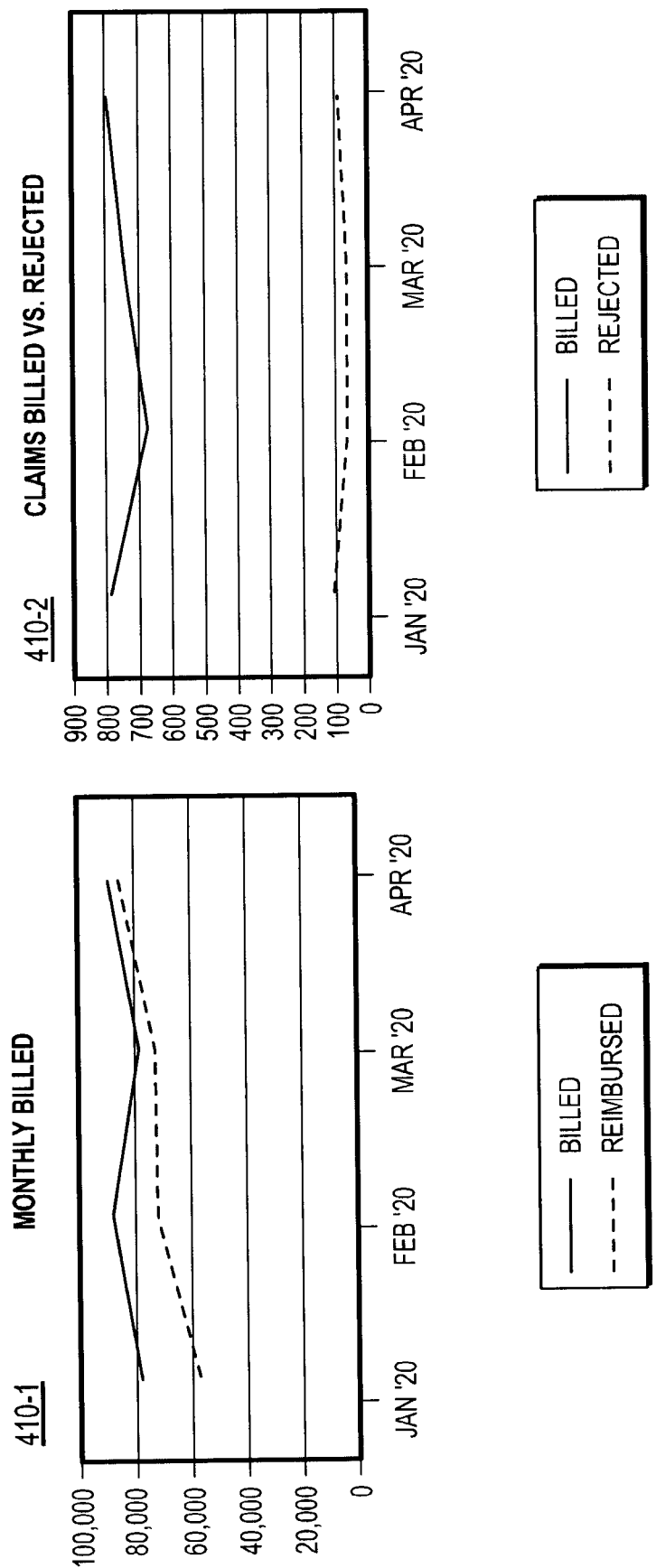
FIG. 4 illustrates screenshots of a reimbursement rate metric in a healthcare system, according to some embodiments.

FIG. 4 illustrates screenshots 410-1 and 410-2 (hereinafter, collectively referred to as "screenshots 410") of a reimbursement rate metric in a healthcare system, according to some embodiments. Screenshot 410-1 illustrates monthly billed amounts and reimbursed amounts, and screenshot 410-2 illustrates number of claims billed and number of claims rejected, over a selected period of time.

Figure 5:
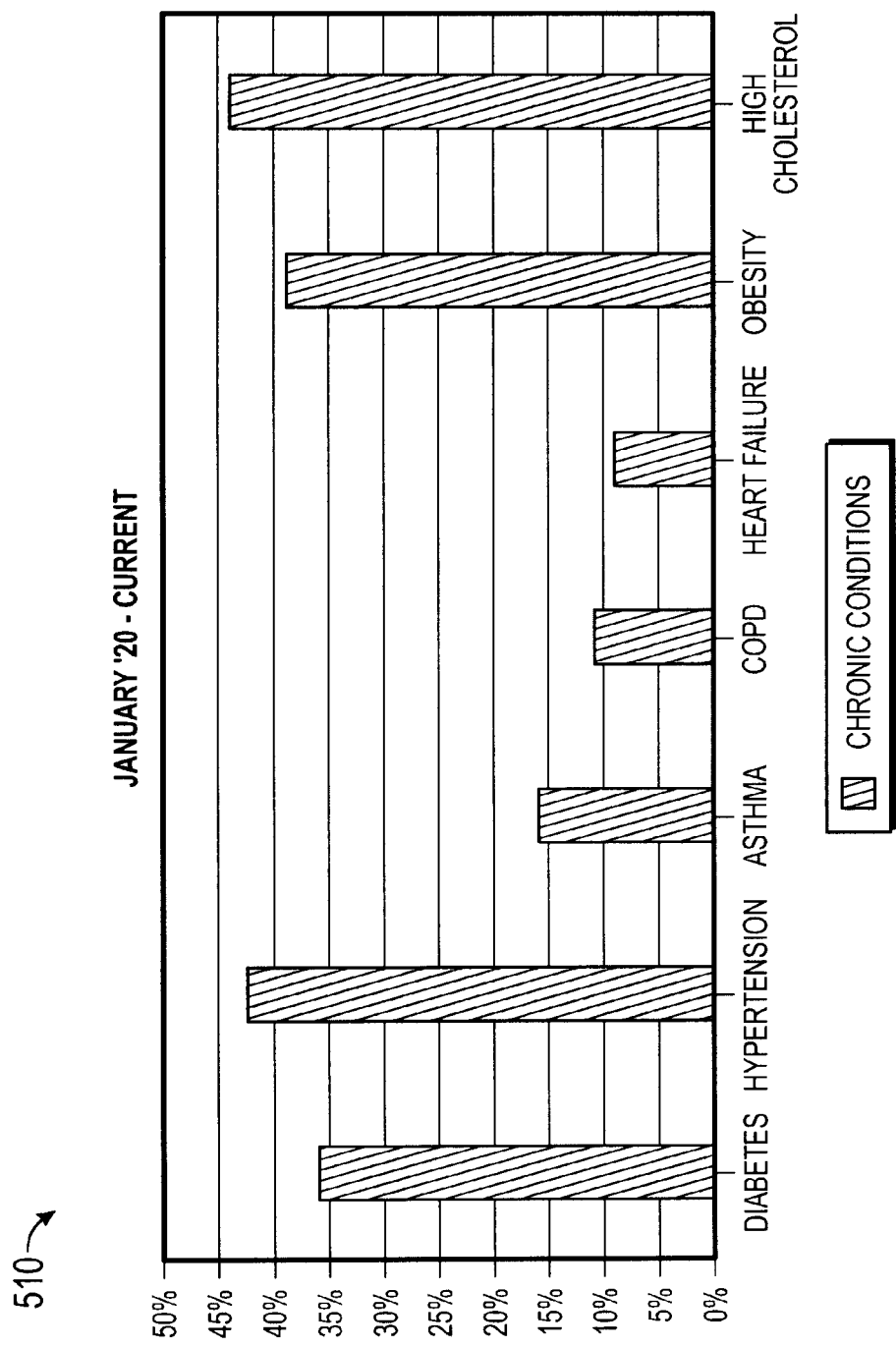
FIG. 5 illustrates a screenshot of a chart for prevalence of chronic conditions in a healthcare system, according to some embodiments.

FIG. 5 illustrates a screenshot 510 of a chart for prevalence of chronic conditions in a healthcare system, according to some embodiments. More specifically, screenshot 510 indicates a number of patients with either of the indicated chronic conditions within a selected time period (e.g., a year), within a cohort of patients.

Figure 6:
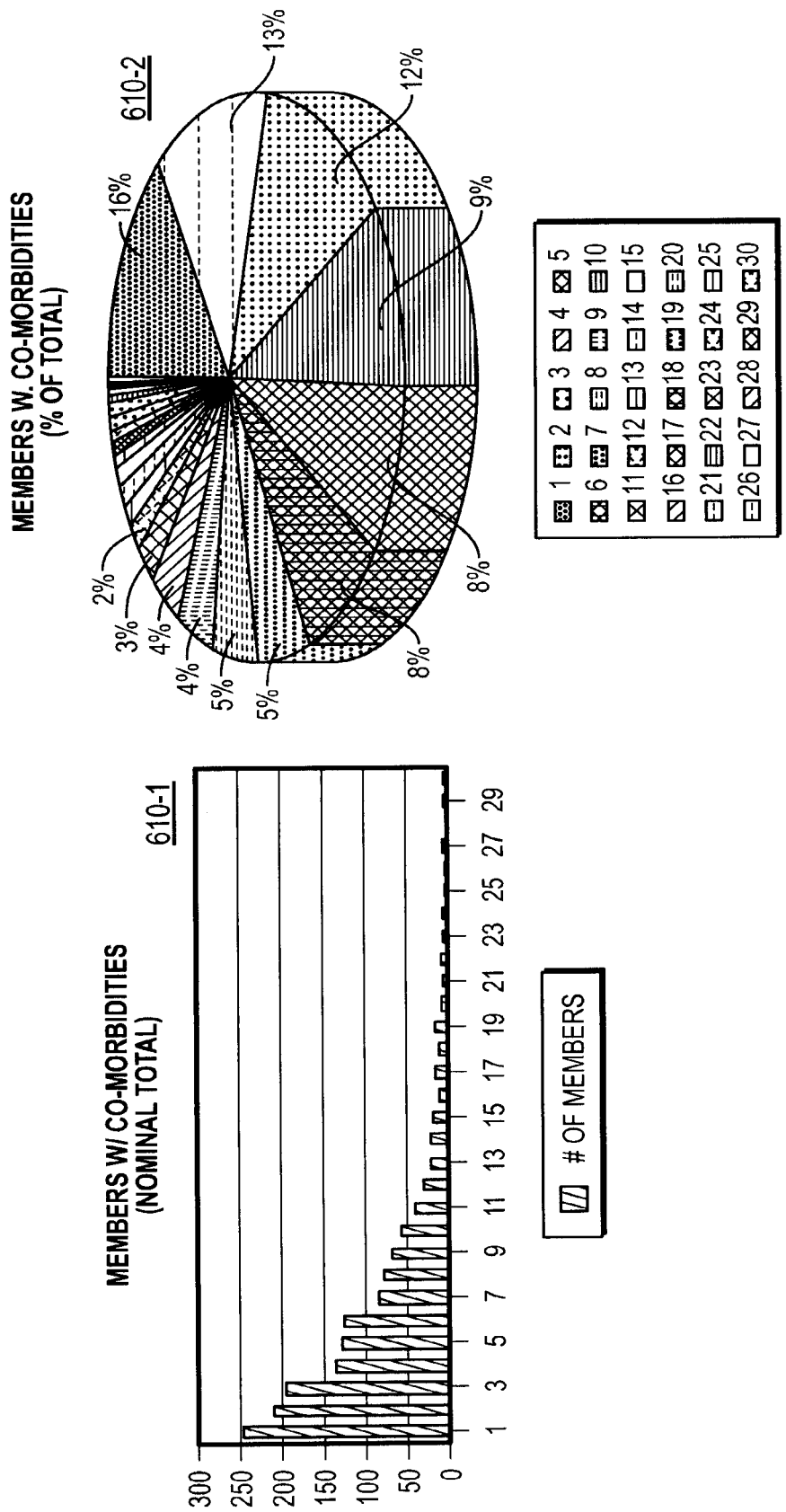
FIG. 6 illustrates a screenshot of charts indicative of an overview of patient conditions in a healthcare system, according to some embodiments.

FIG. 6 illustrates screenshots of charts 610-1 and 610-2 (hereinafter, collectively referred to as "charts 610") indicative of an overview of patient conditions in a healthcare system, according to some embodiments. Chart 610-1 indicates a frequency bar plot for the number of co-morbidities affecting a given number of patients in a selected cohort of patients. Chart 610-2 illustrates the incidence of co-morbidities by percentage of the patient cohort. As expected, patients having none or only one morbidity form larger pools. The degree and slope in which charts 610 decline to fewer co-morbidities for larger patient pools is indicative of the efficiency and effectiveness of a healthcare plan and strategy. A faster drop in charts 610 (fewer co-morbidities for larger pools of patients) is a desirable outcome for a healthcare strategy according to embodiments disclosed herein.

Figure 7:
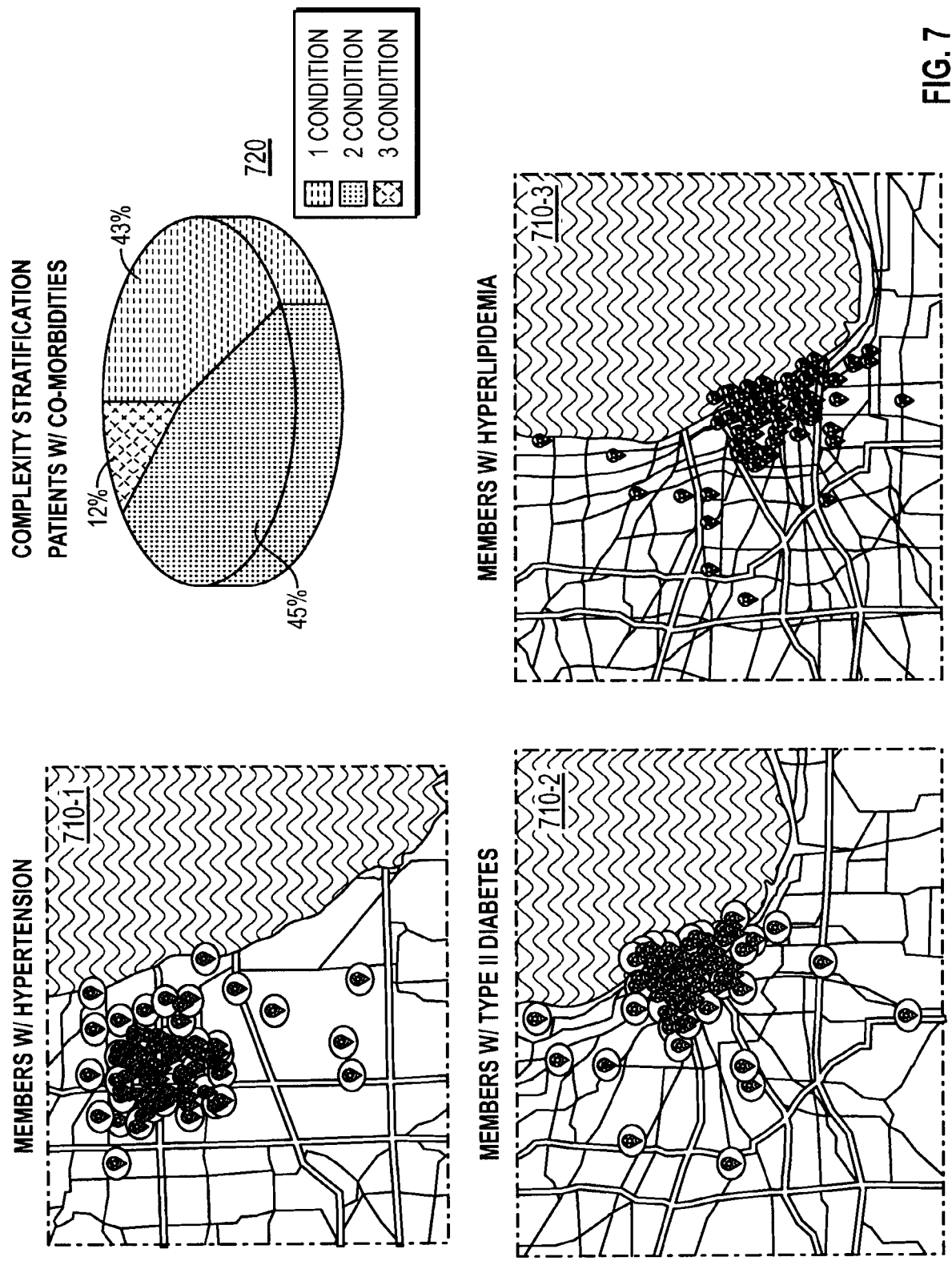
FIG. 7 illustrates screenshots of maps indicative of the geographic distribution of certain chronic conditions over a selected area, according to some embodiments.

FIG. 7 illustrates screenshots of maps 710-1, 710-2, and 710-3 (hereinafter, collectively referred to as "maps 710") indicative of the geographic distribution of certain chronic conditions over a selected area, according to some embodiments. Without loss of generality, map 710-1 illustrates the distribution of Hypertension, map 710-2 illustrates the distribution of Type II Diabetes, and map 710-3 illustrates the distribution of Hyperlipidemia. In some embodiments, a screenshot may include a chart 720 illustrating a complexity stratification of patients with different co-morbidities within a selected cohort.

In some embodiments, maps 710 are selected by finding the most prevalent chronic conditions in a given geographic area. In some embodiments, the user of a value-based decision optimization module as disclosed herein may select the geographic area for maps 710, and also the chronic condition to display. For example, the chronic condition for display may be the most prevalent chronic condition, or a chronic condition shared by a specific patient of interest, or a chronic condition that may result directly from a well identified cause within the geographic area (e.g., a hazardous material spill, a contaminated water source, a contagious disease, and the like).

In some embodiments, a value-based decision optimization module as disclosed herein may display social data associated with a geographic region as illustrated in Table 1, below, in addition to maps 710. The ICD-10 code in Table 1 is the codification for a given chronic disease (e.g., 110 for primary hypertension, E119 for Type II diabetes, E785 for Hyperlipidemia). The highlighted conditions in Table 1 may be those that are directly related to the high level of incidence of the selected chronic condition.

TABLE 1

|    | ICD-10 | Zip Code | Total # of Members |
|----|--------|----------|--------------------|
| 1) | I10    | 60639    | 146                |
| 2) | E119   | 60647    | 96                 |
| 3) | E785   | 60651    | 119                |

| 60651 | 60647 | 60639 |
|-------|-------|-------|
| Neighborhood Safety | Individual Poverty | Neighborhood Safety |
| Violent Crime | Neighborhood Safety | Violent Crime |
| Household Poverty | Adult Binge Drinking | Individual Poverty |
| Community Belonging | Limited English Proficiency | Lack of Formal Education |
| Adult Binge Drinking | Community Belonging | Single Parent Household |
| Individual Poverty | No High School Graduation | Community Belonging |
| No High School Graduation | Household Poverty | Crowded Housing |
| Community Belonging | Adult Smoking | Adult Smoking |
| Limited English Proficiency | Violent Crime | Smoking During Pregnancy |
| Crowded Housing | Individual Poverty | Access to Fruits and Vegetables |
| Adult Smoking | Crowded Housing | Physical Inactivity |
| Easy Access to Fruits & Vegetables | Easy Access to Fruits & Vegetables | Adult Soda Consumption |

Figure 8:
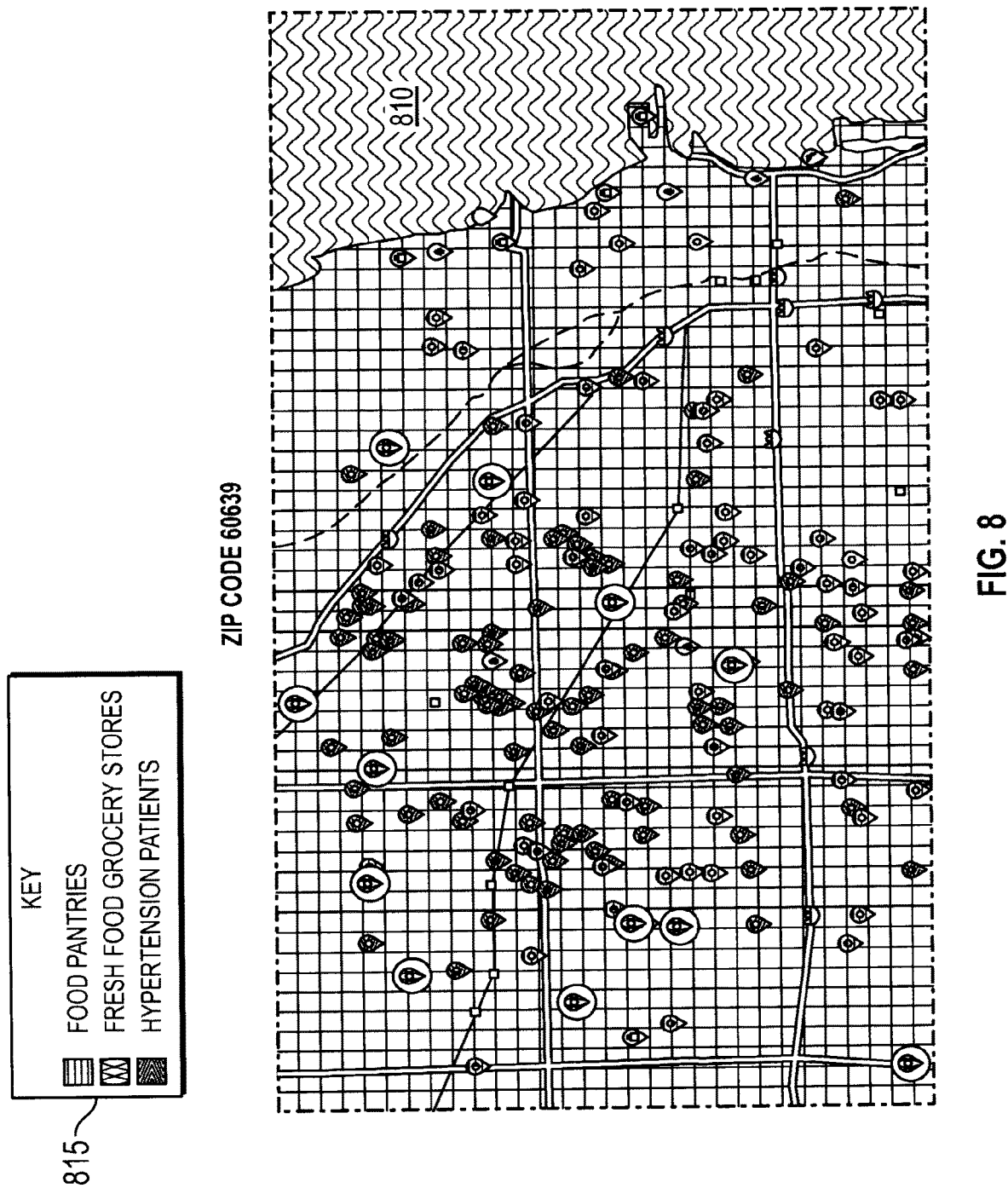
FIG. 8 illustrates a screenshot of a map indicative of resources, opportunities, and certain chronic conditions over a selected area, according to some embodiments.

FIG. 8 illustrates a screenshot of a map 810 indicative of resources, opportunities, and certain chronic conditions over a selected area, according to some embodiments. The screenshot may also include a key 815 indicative of the different elements in map 810. For example, one of the elements may include a distribution of food pantries or fresh food grocery stores in the selected area (e.g., resources), and a distribution of patients with Hypertension in the same area (e.g., among other chronic conditions).

Map 810 is obtained by combining patient demographic data, socioeconomic data, and clinical information. Using map 810 a user of a value-based decision optimization module as disclosed herein may target a specific patient for medical intervention, thus making the healthcare of a cohort of patients much more directed and impactful. For example, map 810 may indicate that a fresh food grocery store is nearby a patient with hypertension, and therefore an opportunity for improvement in the patient condition may be identified. Accordingly, the value-based decision optimization module may recommend the user to advise the patient of the availability of fresh food, or of a nearby food pantry where the patient may find food supplies to improve her/his condition.

Figure 9:
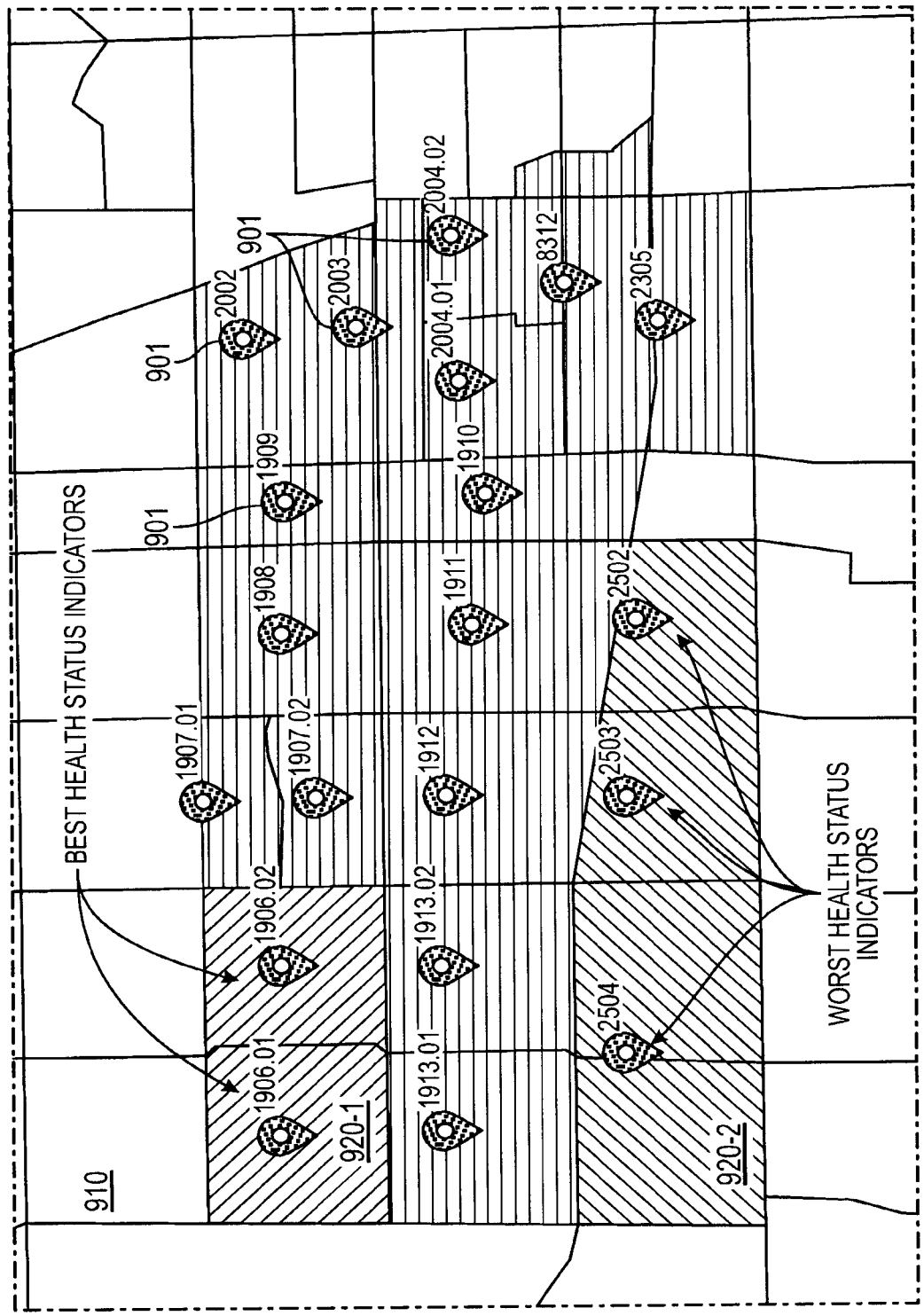
FIG. 9 illustrates a screenshot of a map indicating a distribution of health status over a selected area, according to some embodiments.
Figure 15:
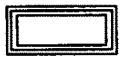
FIG. 15 illustrates a table including social and geographic data for a selected area in a selected cohort of patients, with which the map illustrated in FIG. 9 may be associated, according to some embodiments.
Figure 15:
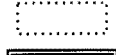
Figure 15:

FIG. 9 illustrates a screenshot of a map 910 indicating a distribution of health status 920-1 and 920-2 (hereinafter, collectively referred to as "health indicators 920") over a selected area, according to some embodiments. Map 910 may be associated with a table including social and geographic data for a selected area in a selected cohort of patients, as illustrated in Table 2 of FIG. 15.

Accordingly, map 910 includes a census tract 901 over the geographic area including a zip code. Health indicators 920 may be illustrated by a diagonal hatching coding (e.g., downward-sloping diagonal hatching for "best health status indicators" 920-1, and upward-sloping diagonal hatching for "worst health status indicators" 920-2). A user may request a value-based decision optimization module as disclosed herein to provide Table 2 of FIG. 15 based on a selected zip code and a selected group of chronic conditions (e.g., Diabetes, Frequent Mental distress, High Blood Pressure, Obesity, Preventive Services Received, Life Expectancy, Income Inequality).

In some embodiments, the user may select a specific census tract to obtain a more detailed listing of possible social factors affecting the healthcare outcome in a specific geographic area (or zip code). Table 3 below illustrates an exemplary table provided by a value-based decision optimization module as disclosed herein.

TABLE 3

| Summary Census Demographic Information | |
|---|---|
| Tract Income Level | Moderate |
| Underserved or Distressed Tract | No |
| 2019 FFIEC Estimated MSA/MD/non-MSA/MD Median Family Income | $82,000 |
| 2019 Estimated Tract Median Family Income | $56,350 |
| 2010 Tract Median Family Income | $51,563 |
| Tract Median Family Income % | 68.72 |
| Tract Population | 5434 |
| Tract Minority % | 86.53 |
| Tract Minority Population | 4702 |
| Owner-Occupied Units | 855 |
| 1- to 4- Family Units | 1412 |
| Census Income Information | |
| Tract Income Level | Moderate |
| 2010 MSA/MD/statewide non-MSA/MD Median Family Income | $75,024 |
| 2019 FFIEC Estimated MSA/MD/non-MSA/MD Median Family Income | $82,000 |
| % below Poverty Line | 12.88 |
| Tract Median Family Income % | 68.72 |
| 2010 Tract Median Family Income | $51,563 |
| 2019 Estimated Tract Median Family Income | $56,350 |
| 2019 Tract Median Household Income | $48,361 |
| Census Population Information | |
| Tract Population | 5434 |
| Tract Minority % | 86.53 |
| Number of Families | 1187 |
| Number of Households | 1386 |
| Non-Hispanic White Population | 732 |
| Tract Minority Population | 4702 |
| American Indian Population | 13 |
| Asian/Hawaiian/Pacific Islander Population | 141 |
| Black Population | 110 |
| Hispanic Population | 4271 |
| Other/Two or More Races Population | 167 |

To obtain Table 3, the value-based decision optimization module may have access to a census data provided by a server handled by a government authority or other public organization. Important indicators may be highlighted in the table, such as the percentage of minority participation in the census tract, a percentage of population below the poverty line, and the like.

Figure 10:
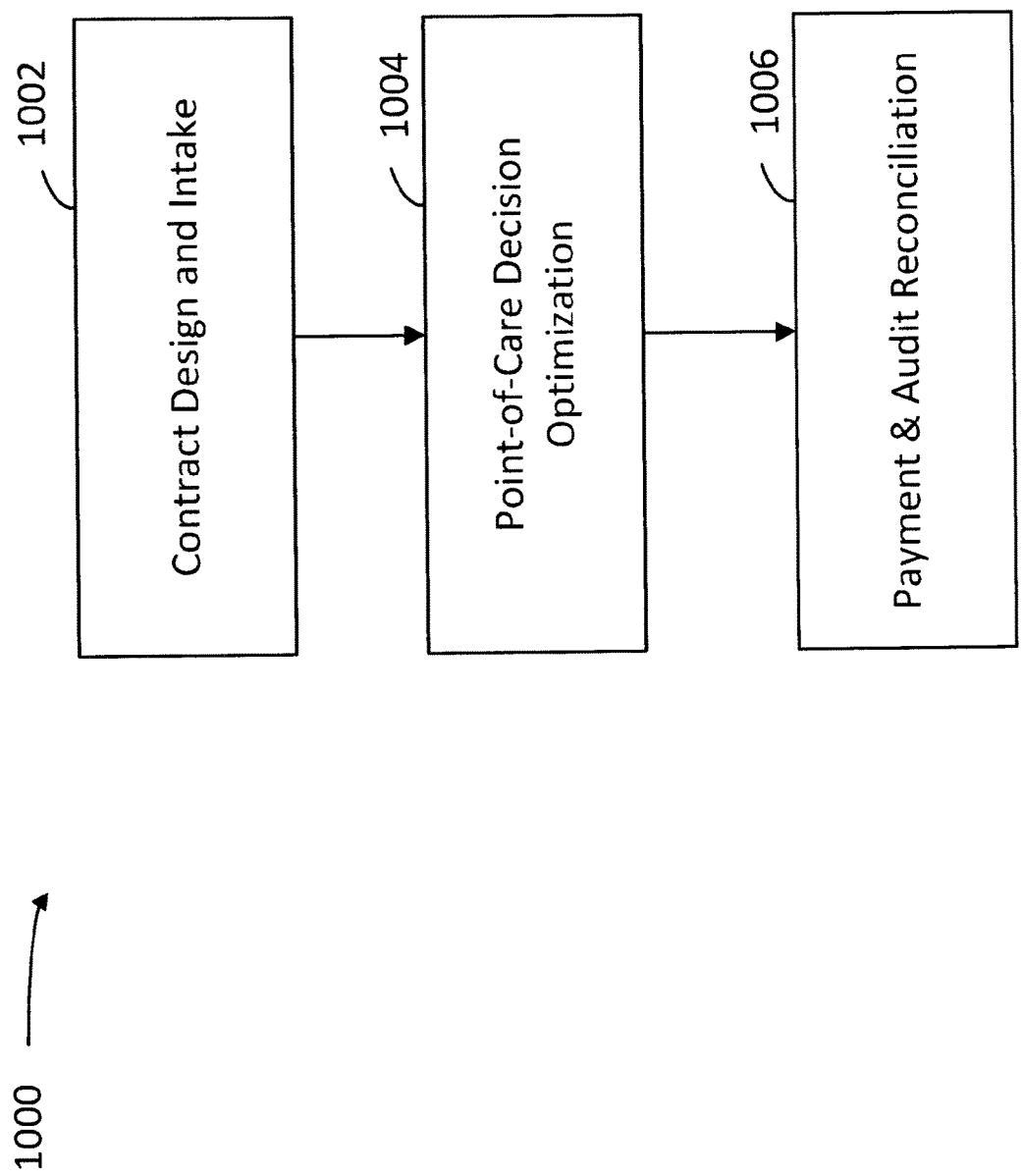
FIG. 10 is a block diagram illustrating components in a value-based system for providing recommendations to improve a healthcare outcome, according to some embodiments.

FIG. 10 is a block diagram 1000 illustrating components in a value-based system for providing recommendations to improve a healthcare outcome, according to some embodiments. Block diagram 1000 includes a contract design and intake block 1002, a point-of-care decision support block 1004, and a payment and audit reconciliation block 1006.

Contract design and intake block 1002 verifies payment efficiency in a contract. In some embodiments, a contract execution strategy is based on current cost/quality performance benchmarks relative to targets for value-based agreements. In some embodiments, contract design and intake block 1002 includes contract quality measures to issue a recommendation to either party in the contract. Point-of-care decision optimization block 1004 provides a value-based decision transparency, and payment and audit reconciliation block 1006 provides risk management to the system. In some embodiments, the system in block diagram 1000 is configured to perform an assessment to a healthcare system for a selected period of time (e.g., 30 days or so). During the selected period of time, each of the blocks in block diagram 1000 has access to healthcare data for clinical, quality, and administrative performance of the system.

Figure 11:
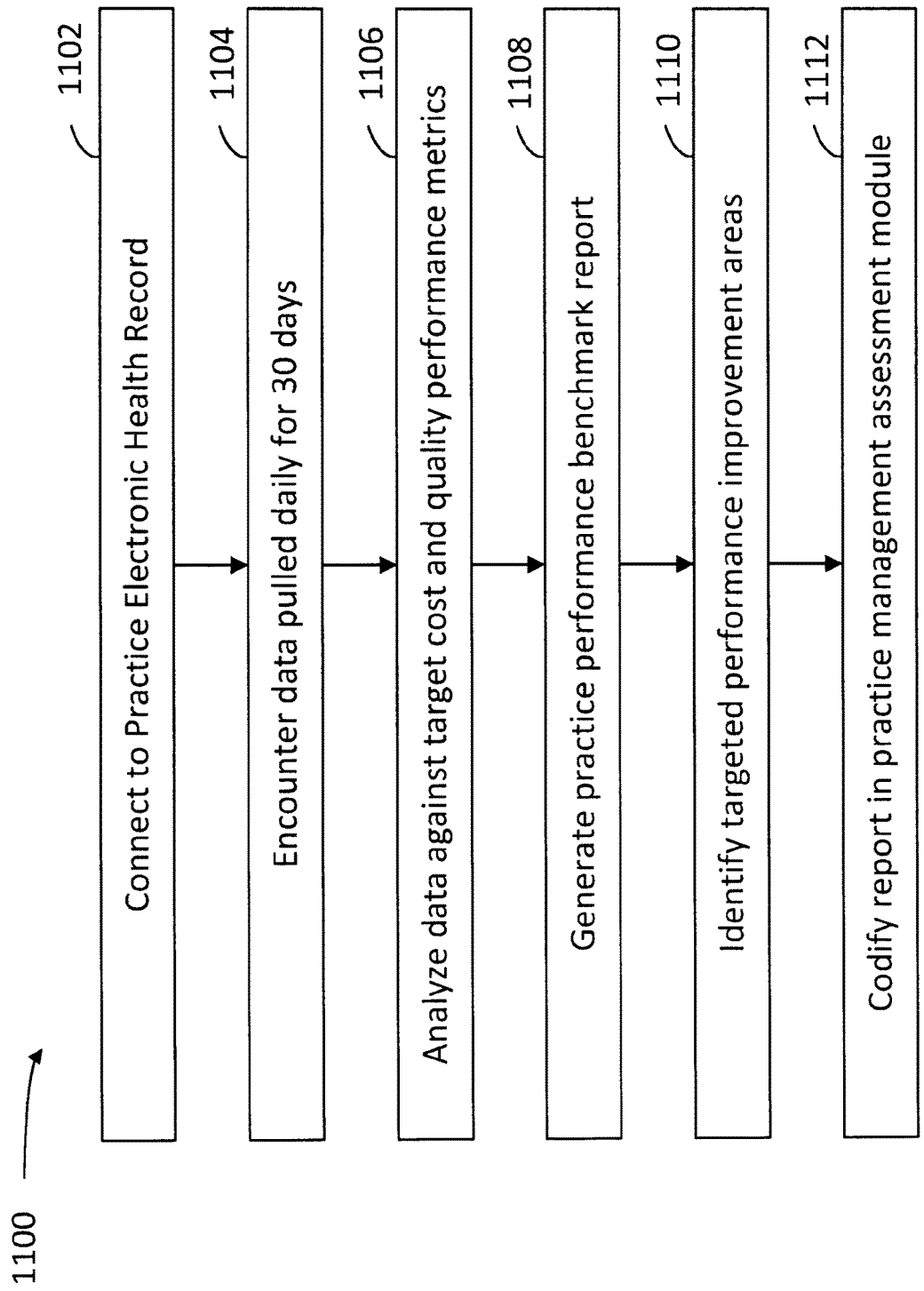
FIG. 11 is a flow chart illustrating steps in a method for optimizing a healthcare outcome using a value-based system, according to some embodiments.

FIG. 11 is a flow chart illustrating steps in a method 1100 for optimizing a healthcare outcome using a value-based system, according to some embodiments. Method 1100 may be at least partially performed by processors executing instructions stored in memories in a client device or a server communicatively coupled through a network, as disclosed herein (e.g., processors 212, memories 220, client device 110, server 130, and network 150). At least one of the memories may include an application installed in the client device, displaying a digital content to a user in an output device of the client device (e.g., application 222, digital content 225, and output device 216). The application may be installed, hosted, and/or managed by a clinical decision engine in the memory of the server (e.g., clinical decision engine 242). The clinical decision engine may also include an electronic health records tool, a point-of-care support tool, and an audit tool (e.g., electronic healthcare records tool 244, point-of-care support tool 246, and audit tool 248). In some embodiments, one or more of the steps in method 1100 may be part of an algorithm including a neural network, a machine learning algorithm, or an artificial intelligence algorithm, as disclosed herein (e.g., algorithm 250). In some embodiments, the clinical decision engine may use social determinants and recommendations provided by a social determinant of a health module or a virtual clinical coordinator module, as disclosed herein (e.g., SDoH module 232 and VCC module 234). In embodiments consistent with the present disclosure, a method may include at least one or more of the steps in method 1100 performed in a different order, or simultaneously, quasi-simultaneously, or overlapping in time.

Step 1102 includes connecting to a practice electronic health record.

Step 1104 includes encountering data pulled daily for thirty (30) days, or so. In some embodiments, the period of time for pulling daily data may be more or less than 30 days, depending on a degree of certainty desired for a recommendation.

Step 1106 includes analyzing data against target performance metrics. In some embodiments, step 1106 includes analyzing data against target cost and quality performance metrics. The target performance metrics may be established in a contract between the healthcare provider and the payor. In some embodiments, the target performance metrics may include a government benchmark, a medical benchmark, or a clinical benchmark.

Step 1108 includes generating a practice performance benchmark report. In some embodiments, the report may include an evaluation as to whether or not one or more of the benchmarks have been achieved or satisfied, and to what degree.

Step 1110 includes identifying targeted performance improvement areas. In some embodiments, step 1110 includes identifying a benchmark that is not fully satisfied and determining one or more actions that may improve the benchmark results.

Step 1112 includes codifying a report in a practice management assessment module. In some embodiments, step 1112 may include providing the report to the user, e.g., a healthcare provider, a physician, a clinic manager, and the like.

Figure 12:
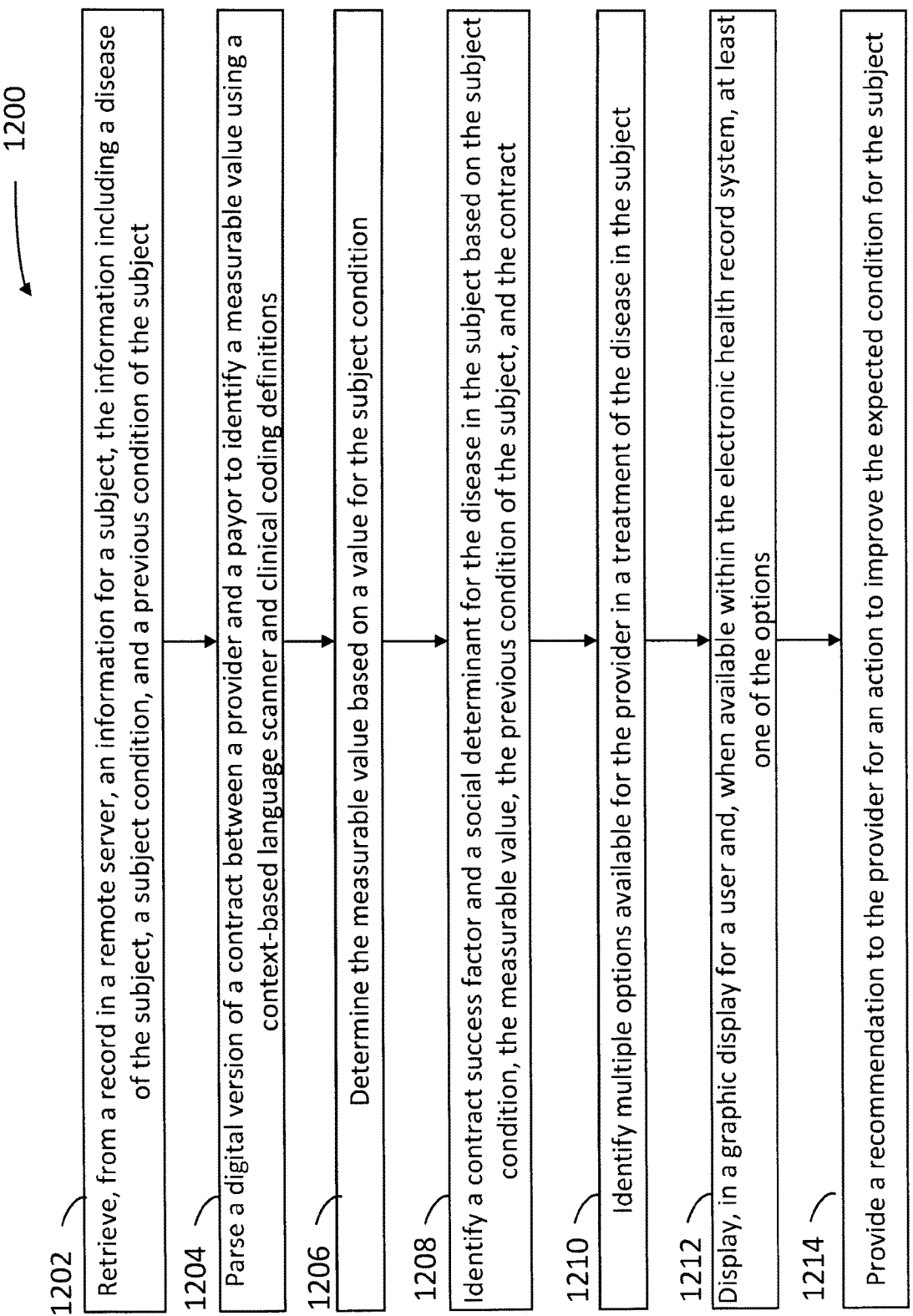
FIG. 12 is a flow chart illustrating steps in a method for providing a recommendation to a healthcare provider in a value-based system, according to some embodiments.

FIG. 12 is a flow chart illustrating steps in a method 1200 for providing a recommendation to a healthcare provider in a value-based system, according to some embodiments. Method 1200 may be at least partially performed by processors executing instructions stored in memories in a client device or a server communicatively coupled through a network, as disclosed herein (e.g., processors 212, memories 220, client device 110, server 130, and network 150). At least one of the memories may include an application installed in the client device, displaying a digital content to a user in an output device of the client device (e.g., application 222, digital content 225, and output device 216). The application may be installed, hosted, and/or managed by a clinical decision engine in the memory of the server (e.g., clinical decision engine 242). The clinical decision engine may also include an electronic health records tool, a point-of-care support tool, and an audit tool (e.g., electronic healthcare records tool 244, point-of-care support tool 246, and audit tool 248). In some embodiments, one or more of the steps in method 1200 may be part of an algorithm including a neural network, a machine learning algorithm, or an artificial intelligence algorithm, as disclosed herein (e.g., algorithm 250). In some embodiments, the clinical decision engine may use social determinants and recommendations provided by a social determinant of a health module or a virtual clinical coordinator module, as disclosed herein (e.g., SDoH module 232 and VCC module 234). In embodiments consistent with the present disclosure, a method may include at least one or more of the steps in method 1200 performed in a different order, or simultaneously, quasi-simultaneously, or overlapping in time.

Step 1202 includes retrieving, from a record in a remote server, an information for a subject, the information including a disease of the subject, a subject condition, and a previous condition of the subject. In some embodiments, the information for the subject is a health information for the subject, the health information including a health history of the subject. In some embodiments, the health information includes a location residence of the subject and a statistical information regarding an incidence of the disease in the subject in an area including the location residence of the subject, and step 1202 further includes causing a display in a client device to display a chart indicative of the statistical information. In some embodiments, retrieving the health information includes identifying one or more diseases affecting most inhabitants in a location that includes a residence of the subject.

Step 1204 includes parsing a digital version of a contract between a provider and a payor to identify a measurable value using a context-based language scanner.

Step 1206 includes determining the measurable value based on a value for the subject condition.

Step 1208 includes identifying a contract success factor and a social determinant for the disease of the subject based on the subject condition, the health history of the subject, and the health contract. In some embodiments, step 1208 further includes retrieving a social information from the subject, identifying, from the social information, multiple census tracts, at least one census track including a demographic parameter of the subject, and identifying the social determinant based on the demographic parameter of the subject. In some embodiments, step 1208 includes aggregating a prevalent disease condition for multiple patients in an area that includes a patient residence. In some embodiments, step 1208 further includes displaying, for a user, a map of an area that includes a patient residence, a prevalent disease in the area, and a location of a food supply for providing the recommendation to the healthcare provider. In some embodiments, step 1208 further includes providing, for a user, a tabulated display of multiple patients including a demographic parameter of the subject for providing the recommendation to the healthcare provider.

Step 1210 includes identifying multiple options available for the healthcare provider in a treatment of the disease in the subject. In some embodiments, step 1210 includes evaluating a performance parameter for the healthcare provider based on the subject condition. In some embodiments, step 1210 includes identifying an expected outcome for the subject based on the performance parameter and on the disease of the subject. In some embodiments, step 1210 includes correlating a current condition of the subject with a statistical information including an outcome for a cohort of people including the subject.

Step 1212 includes displaying, in a graphic display for a user, at least one of the options. In some embodiments, step 1212 includes, when available or when selected by the user, displaying within the electronic health record system at least one of the options.

Step 1214 includes providing a recommendation to the healthcare provider for an action to improve the expected outcome for the subject. In some embodiments, the health information includes a location of a food supply for the subject in an area including a residence location of the subject, and step 1214 includes indicating a location of a nearby food supply for the subject. In some embodiments, the health information includes a location of residence of the subject and step 1214 includes recommending the subject to perform a physical activity based on an availability of a sports club in a vicinity of the location of residence. In some embodiments, step 1214 further includes measuring a frequency of adopting the recommendation by the healthcare provider, to optimize the performance parameter. In some embodiments, step 1214 further includes selecting the action to improve the expected outcome for the subject based on a historic performance with a cohort of subjects sharing a demographic trait with the subject. In some embodiments, step 1214 further includes assessing a cost of a healthcare procedure on the subject and providing the recommendation to the healthcare provider based on the cost of the healthcare procedure. In some embodiments, step 1214 further includes recommending a healthcare diagnostic procedure for the subject. In some embodiments, step 1214 further includes identifying a resource available to the subject for providing the recommendation.

Figure 13:
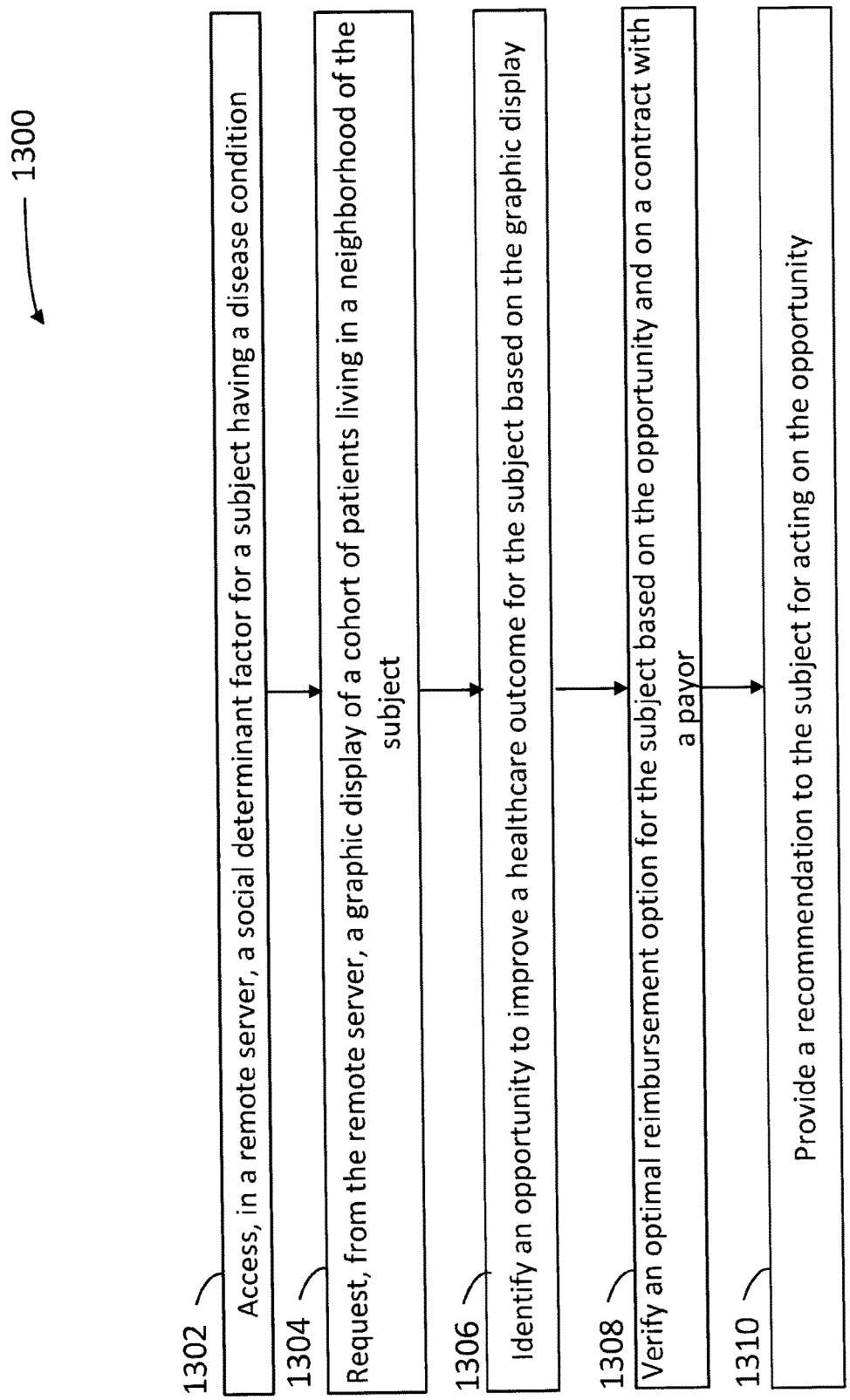
FIG. 13 is a flow chart illustrating steps in a method for providing recommendations in a value-based optimization healthcare system, according to some embodiments.

FIG. 13 is a flow chart illustrating steps in a method 1300 for providing recommendations in a value-based optimization healthcare system, according to some embodiments. Method 1300 may be at least partially performed by processors executing instructions stored in memories in a client device or a server communicatively coupled through a network, as disclosed herein (e.g., processors 212, memories 220, client device 110, server 130, and network 150). At least one of the memories may include an application installed in the client device, displaying a digital content to a user in an output device of the client device (e.g., application 222, digital content 225, and output device 216). The application may be installed, hosted, providing recommendations in a value-based optimization healthcare system and/or managed by a clinical decision engine in the memory of the server (e.g., clinical decision engine 242). The clinical decision engine may also include an electronic health records tool, a point-of-care support tool, and an audit tool (e.g., electronic healthcare records tool 244, point-of-care support tool 246, and audit tool 248). In some embodiments, one or more of the steps in method 1300 may be part of an algorithm including a neural network, a machine learning algorithm, or an artificial intelligence algorithm, as disclosed herein (e.g., algorithm 250). In some embodiments, the clinical decision engine may use social determinants and recommendations provided by a social determinant of a health module or a virtual clinical coordinator module, as disclosed herein (e.g., SDoH module 232 and VCC module 234). In embodiments consistent with the present disclosure, a method may include at least one or more of the steps in method 1300 performed in a different order, or simultaneously, quasi-simultaneously, or overlapping in time.

Step 1302 includes accessing, in a remote server, a social determinant factor for a subject having a disease condition.

Step 1304 includes requesting, from the remote server, a graphic display of a cohort of patients living in a neighborhood of the subject.

Step 1306 includes identifying an opportunity to improve a healthcare outcome for the subject based on the graphic display.

Step 1308 includes verifying an optimal reimbursement option for the subject based on the opportunity and on a contract with a payor. In some embodiments, step 1308 includes verifying a payment option for the subject based on the opportunity and on a contract with a payor.

Step 1310 includes providing a recommendation to the subject for acting on the opportunity.

Hardware Overview

Figure 14:
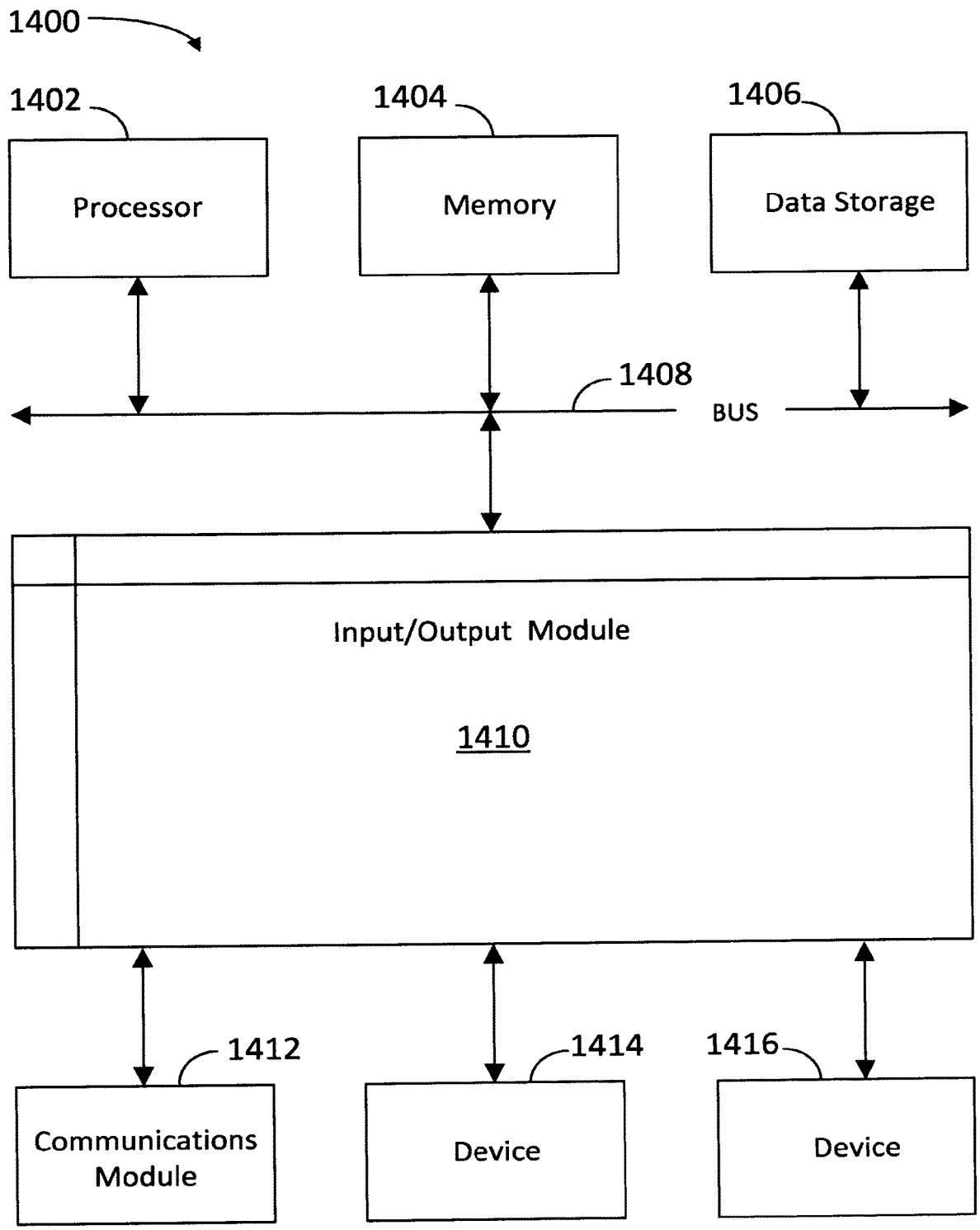
FIG. 14 is a block diagram illustrating an example computer system with which the client and server of FIGS. 1 and 2 and the methods of FIGS. 11, 12 and 13 can be implemented.

FIG. 14 is a block diagram illustrating an exemplary computer system 1400 with which client device 110 and servers 130 of FIGS. 1 and 2, and the methods of FIGS. 11, 12, and 13 can be implemented. In certain aspects, the computer system 1400 may be implemented using hardware or a combination of software and hardware, either in a dedicated server, or integrated into another entity, or distributed across multiple entities.

Computer system 1400 (e.g., client device 110 and server 130) includes a bus 1408 or other communication mechanism for communicating information, and a processor 1402 (e.g., processors 212) coupled with bus 1408 for processing information. By way of example, the computer system 1400 may be implemented with one or more processors 1402. Processor 1402 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 1400 can include, in addition to hardware, code that creates an execution environment for the computer program in question, e.g., code that constitutes processor firmware, a protocol stack, a database management system, an operating system, or a combination of one or more of them stored in an included memory 1404 (e.g., memories 220), such as a Random Access Memory (RAM), a flash memory, a Read-Only Memory (ROM), a Programmable Read-Only Memory (PROM), an Erasable PROM (EPROM), registers, a hard disk, a removable disk, a CD-ROM, a DVD, or any other suitable storage device, coupled with bus 1408 for storing information and instructions to be executed by processor 1402. The processor 1402 and the memory 1404 can be supplemented by, or incorporated in, special purpose logic circuitry.

The instructions may be stored in the memory 1404 and implemented in one or more computer program products, e.g., one or more modules of computer program instructions encoded on a computer-readable medium for execution by, or to control the operation of, the computer system 1400, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and xml-based languages. Memory 1404 may also be used for storing temporary variable or other intermediate information during execution of instructions to be executed by processor 1402.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and inter-coupled by a communication network. The processes and logic flows described in this specification can be performed by one or more programmable processors executing one or more computer programs to perform functions by operating on input data and generating output.

Computer system 1400 further includes a data storage device 1406 such as a magnetic disk or optical disk, coupled with bus 1408 for storing information and instructions. Computer system 1400 may be coupled via input/output module 1410 to various devices. Input/output module 1410 can be any input/output module. Exemplary input/output modules 1410 include data ports such as USB ports. The input/output module 1410 is configured to connect to a communications module 1412. Exemplary communications modules 1412 (e.g., communications modules 218) include networking interface cards, such as Ethernet cards and modems. In certain aspects, input/output module 1410 is configured to connect to a plurality of devices, such as an input device 1414 (e.g., input device 214) and/or an output device 1416 (e.g., output device 216). Exemplary input devices 1414 include a keyboard and a pointing device, e.g., a mouse or a trackball, by which a patient can provide input to the computer system 1400. Other kinds of input devices 1414 can be used to provide for interaction with a patient as well, such as a tactile input device, visual input device, audio input device, or brain-computer interface device. For example, feedback provided to the patient can be any form of sensory feedback, e.g., visual feedback, auditory feedback, or tactile feedback; and input from the patient can be received in any form, including acoustic, speech, tactile, or brain wave input. Exemplary output devices 1416 include display devices, such as an LCD (liquid crystal display) monitor, for displaying information to the patient.

According to one aspect of the present disclosure, the client device 110 and server 130 can be implemented using a computer system 1400 in response to processor 1402 executing one or more sequences of one or more instructions contained in memory 1404. Such instructions may be read into memory 1404 from another machine-readable medium, such as data storage device 1406. Execution of the sequences of instructions contained in main memory 1404 causes processor 1402 to perform the process steps described herein. One or more processors in a multi-processing arrangement may also be employed to execute the sequences of instructions contained in memory 1404. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., a data server, or that includes a middleware component, e.g., an application server, or that includes a front end component, e.g., a client computer having a graphical patient interface or a Web browser through which a patient can interact with an implementation of the subject matter described in this specification, or any combination of one or more such back end, middleware, or front end components. The components of the system can be intercoupled by any form or medium of digital data communication, e.g., a communication network. The communication network (e.g., network 150) can include, for example, any one or more of a LAN, a WAN, the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computer system 1400 can include clients and servers. A client and server are generally remote from each other and typically interact through a communication network. The relationship of client and server arises by virtue of computer programs running on the respective computers and having a client-server relationship to each other. Computer system 1400 can be, for example, and without limitation, a desktop computer, laptop computer, or tablet computer. Computer system 1400 can also be embedded in another device, for example, and without limitation, a mobile telephone, a PDA, a mobile audio player, a Global Positioning System (GPS) receiver, a video game console, and/or a television set top box.

The term "machine-readable storage medium" or "computer-readable medium" as used herein refers to any medium or media that participates in providing instructions to processor 1402 for execution. Such a medium may take many forms, including, but not limited to, non-volatile media, volatile media, and transmission media. Non-volatile media include, for example, optical or magnetic disks, such as data storage device 1406. Volatile media include dynamic memory, such as memory 1404. Transmission media include coaxial cables, copper wire, and fiber optics, including the wires forming bus 1408. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

To illustrate the interchangeability of hardware and software, items such as the various illustrative blocks, modules, components, methods, operations, instructions, and algorithms have been described generally in terms of their functionality. Whether such functionality is implemented as hardware, software, or a combination of hardware and software depends upon the particular application and design constraints imposed on the overall system. Skilled artisans may implement the described functionality in varying ways for each particular application.

As used herein, the phrase "at least one of" preceding a series of items, with the terms "and" or "or" to separate any of the items, modifies the list as a whole, rather than each member of the list (e.g., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The word "exemplary" is used herein to mean "serving as an example, instance, or illustration." Any embodiment described herein as "exemplary" is not necessarily to be construed as preferred or advantageous over other embodiments. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, and other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public, regardless of whether such disclosure is explicitly recited in the above description. No clause element is to be construed under the provisions of 35 U.S.C. § 112, sixth paragraph, unless the element is expressly recited using the phrase "means for" or, in the case of a method clause, the element is recited using the phrase "step for."

While this specification contains many specifics, these should not be construed as limitations on the scope of what may be described, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially described as such, one or more features from a described combination can in some cases be excised from the combination, and the described combination may be directed to a subcombination or variation of a subcombination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the described subject matter requires more features than are expressly recited in each clause. Rather, as the claims reflect, inventive subject matter lies in less than all features of a single disclosed configuration or operation. The claims are hereby incorporated into the detailed description, with each clause standing on its own as a separately described subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A computer-implemented method, comprising:
   retrieving, from an electronic health record, an information for a subject, the information comprising a condition of the subject and a geographic location of the subject;
   identifying a patient cohort for the subject, based on the information for the subject;
   retrieving, from the electronic health record, a list of chronic conditions for the patient cohort sorted by an incidence level in the geographic location;
   evaluating a determinant factor in the condition of the subject, based on the list of the chronic conditions;
   identifying one or more resources for resolving the determinant factor available in the geographic location;
   identifying a healthcare success factor based on an availability of the one or more resources for the subject and an inverse correlation between a number of patients in the patient cohort and a number of co-morbidities affecting the number of patients;
   identifying an expected condition for the subject based on the healthcare success factor and a historic performance with the patient cohort associated with the condition of the subject;
   identifying a plurality of actions to be performed by the subject to improve the expected condition for the subject;
   receiving, via a user interface of a client device associated with a provider, a selection of a first action of the plurality of actions; and
   directing the provider, via an electronic communication, to request an access to a resource of the one or more resources, the resource including a facility supporting the first action.

2. The computer-implemented method of claim 1, further comprising causing a display in a client device to display a map of the geographic location, the map being indicative of the incidence level of the chronic conditions.

3. The computer-implemented method of claim 1, wherein retrieving the information comprises identifying one or more diseases affecting most inhabitants in the geographic location.

4. The computer-implemented method of claim 1, wherein the resources include a food supply for the subject in the geographic location.

5. The computer-implemented method of claim 1, wherein the resources include a sports facility.

6. The computer-implemented method of claim 1, wherein identifying the healthcare success factor comprises correlating a current condition of the subject with a statistical information including an outcome for the patient cohort.

7. The computer-implemented method of claim 1, wherein the information for the subject comprises a social information, further comprising identifying, from the social information, multiple census tracts and evaluating the determinant factor in the condition of the subject comprises identifying a demographic parameter from at least one of the census tracts.

8. The computer-implemented method of claim 1, wherein evaluating the determinant factor comprises aggregating a prevalent disease condition for multiple patients in the geographic location.

9. The computer-implemented method of claim 1, further comprising displaying, for a user, a map of the geographic location, the map indicative of a location for each of the one or more resources.

10. The computer-implemented method of claim 1, further comprising providing, for a user, a tabulated display of a statistical analysis of medical data and determinant factors for multiple subjects in the patient cohort.

11. The computer-implemented method of claim 1, further comprising measuring a frequency of the provider selecting the first action.

12. The computer-implemented method of claim 1, further comprising selecting the plurality of actions to improve the expected condition for the subject based on a previous performance with a cohort of subjects sharing a demographic trait with the subject.

13. The computer-implemented method of claim 1, further comprising determining, for the patient cohort, a co-morbidity chart indicative of a percentage of the patient cohort sharing one or more conditions with the subject, wherein the healthcare success factor is commensurate with a negative slope of the co-morbidity chart indicating the inverse correlation between the number of patients in the patient cohort and the number of co-morbidities affecting the number of patients.

14. A system, comprising:
a memory configured to store multiple instructions; and
one or more processors configured to execute the instructions to cause the system to:
retrieve, from an electronic health record, an information for a subject, the information comprising a condition of the subject and a geographic location of the subject;
identify a patient cohort for the subject, based on the information for the subject;
retrieve, from the electronic health record, a list of chronic conditions for the patient cohort sorted by an incidence level in the geographic location;
evaluate a determinant factor in the condition of the subject, based on the list of the chronic conditions;
identify one or more resources for resolving the determinant factor available in the geographic location;
identify a healthcare success factor based on an availability of the one or more resources for the subject and an inverse correlation between a number of patients in the patient cohort and a number of co-morbidities affecting the number of patients;
identify an expected condition for the subject based on the healthcare success factor and a historic performance with the patient cohort associated with the condition of the subject;
identify a plurality of actions to be performed by the subject to improve the expected condition for the subject;
receive, via a user interface of a client device associated with a provider, a selection of a first action of the plurality of actions; and
direct the provider, via an electronic communication, to request an access to a resource of the one or more resources, the resource including a facility supporting the first action.

15. The system of claim 14, wherein the one or more processors further execute instructions to cause a display in a client device to display a map of the geographic location, the map being indicative of the incidence level of the chronic conditions.

16. The system of claim 14, wherein to retrieve the information the one or more processors execute instructions to identify one or more diseases affecting most inhabitants in the geographic location.

17. The system of claim 14, wherein the resources include a food supply for the subject in the geographic location.

18. The system of claim 14, wherein the resources include a sports facility.

19. The system of claim 14, wherein to identify the healthcare success factor the one or more processors execute instructions to correlate a current condition of the subject with a statistical information including an outcome for the patient cohort.

20. A non-transitory computer-readable storage medium comprising instructions stored thereon, which when executed by one or more processors, cause the one or more processors to perform a method, the method comprising:
retrieving, from an electronic health record, an information for a subject, the information comprising a condition of the subject and a geographic location of the subject;
identifying a patient cohort for the subject, based on the information for the subject;
retrieving, from the electronic health record, a list of chronic conditions for the patient cohort sorted by an incidence level in the geographic location;
evaluating a determinant factor in the condition of the subject, based on the list of the chronic conditions;
identifying one or more resources for resolving the determinant factor available in the geographic location;
identifying a healthcare success factor based on an availability of the one or more resources for the subject and an inverse correlation between a number of patients in the patient cohort and a number of co-morbidities affecting the number of patients;
identifying an expected condition for the subject based on the healthcare success factor and a historic performance with the patient cohort associated with the condition of the subject;
identifying a plurality of actions to be performed by the subject to improve the expected condition for the subject;
receiving, via a user interface of a client device associated with a provider, a selection of a first action of the plurality of actions; and
directing the provider, via an electronic communication, to request an access to a resource of the one or more resources, the resource including a facility supporting the first action.

* * * * *